US011317870B1

(12) United States Patent
De Sapio et al.

(10) Patent No.: US 11,317,870 B1
(45) Date of Patent: May 3, 2022

(54) SYSTEM AND METHOD FOR HEALTH ASSESSMENT ON SMARTPHONES

(71) Applicant: HRL Laboratories, LLC, Malibu, CA (US)

(72) Inventors: Vincent De Sapio, Westlake Village, CA (US); Jaehoon Choe, Agoura Hills, CA (US); Iman Mohammadrezazadeh, Los Angeles, CA (US); Kang-Yu Ni, Calabasas, CA (US); Heiko Hoffmann, Simi Valley, CA (US); Charles E. Martin, Santa Monica, CA (US); Yuri Owechko, Newbury Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 646 days.

(21) Appl. No.: 16/267,376

(22) Filed: Feb. 4, 2019

Related U.S. Application Data

(63) Continuation-in-part of application No. 16/034,780, filed on Jul. 13, 2018, now Pat. No. 10,726,311, and
(Continued)

(51) Int. Cl.
*A61B 5/00* (2006.01)
*A61B 5/11* (2006.01)

(52) U.S. Cl.
CPC .......... *A61B 5/6898* (2013.01); *A61B 5/0077* (2013.01); *A61B 5/1112* (2013.01);
(Continued)

(58) Field of Classification Search
None
See application file for complete search history.

(56) References Cited

U.S. PATENT DOCUMENTS 7,024,399 B2 * 4/2006 Sumner, II ............. G16H 50/50
706/45
8,204,988 B2 6/2012 Lin et al.
(Continued)

FOREIGN PATENT DOCUMENTS

WO WO2017-044082 A1 3/2017
WO WO2017-111832 A1 6/2017

OTHER PUBLICATIONS

Viswanathan et al., Research Challenges in Computation, Communication, and Context Awareness for Ubiquitous Healthcare, IEEE Communications Magazine, May 2012.*
(Continued)

*Primary Examiner* — Catherine T. Rastovski
(74) *Attorney, Agent, or Firm* — Tope-McKay & Associates

(57) ABSTRACT

Described is a system for health assessment. The system is implemented on a mobile device having at least one of an accelerometer, a geographic location sensor, and a camera. In operation, the system obtains sensor data related to an operator of the mobile device from one of the sensors. A network of networks (NoN) is generated based on the sensor data, the NoN having a plurality of layers with linked nodes. Tuples are thereafter generated. Each tuple contains a node from each layer that optimizes importance, diversity, and coherence. Storylines are created based on the tuples that solves a longest path problem for each tuple. The storylines track multiple symptom progressions of the operator. Finally, a disease prediction of the operator is provided based on the storylines.

18 Claims, 16 Drawing Sheets

Related U.S. Application Data a continuation-in-part of application No. 16/118,161, filed on Aug. 30, 2018, now Pat. No. 11,194,330.

(60) Provisional application No. 62/627,123, filed on Feb. 6, 2018, provisional application No. 62/581,625, filed on Nov. 3, 2017, provisional application No. 62/558,094, filed on Sep. 13, 2017.

(52) U.S. Cl.
CPC .......... *A61B 5/1118* (2013.01); *A61B 5/7267* (2013.01); *A61B 5/7275* (2013.01); *A61B 2562/0219* (2013.01); *A61B 2562/06* (2013.01)

(56) References Cited

U.S. PATENT DOCUMENTS

| | | |
|---|---|---|
| 2015/0296214 A1 | 10/2015 | Mahfoodh et al. |
| 2016/0148103 A1* | 5/2016 | Sarrafzadeh ........... G06K 9/469 706/46 |
| 2017/0168991 A1 | 6/2017 | Baskaran et al. |
| 2018/0285699 A1 | 10/2018 | Kolouri et al. |

OTHER PUBLICATIONS

Notification of Transmittal of International Search Report and the Written Opinion of the International Searching Authority for PCT/US2018/042008; dated Nov. 26, 2018.

International Search Report of the International Searching Authority for PCT/US2018/042008; dated Nov. 26, 2018.

Written Opinion of the International Searching Authority for PCT/US2018/042008; dated Nov. 26, 2018.

Guoxu Zhou et al., 'Linked Component Analysis From Matrices to High-Order Tensors: Applications to Biomedical Data', In: Proceedings of the IEEE, vol. 104, Issue 2, Feb. 2016.

Sotiras, Aristeidis, Susan M. Resnick, and Christos Davatzikos. "Finding imaging patterns of structural covariance via non-negative matrix factorization." NeuroImage 108 (2015): pp. 1-16.

Simonyan, Karen, and Andrew Zisserman. "Very deep convolutional networks for large-scale image recognition." arXiv preprint arXiv:1409.1556, pp. 1-14, (2014).

T. Lindeberg, "Scale-space theory in computer vision", vol. 256. Springer Science & Business Media, 2013. Chapter 7. pp. 165-170.

Xie, Junyuan, Ross Girshick, and Ali Farhadi. "Unsupervised Deep Embedding for Clustering Analysis." arXiv preprint arXiv:1511.06335, pp. 1-10, (2015).

B. Zhou, A. Khosla, A. Lapedriza, A. Oliva, and A. Torralba. "Object detectors emerge in deep scene CNNs." arXiv preprint arXiv:1412.6856, pp. 1-12, 2014.

A. Gonzalez-Garcia, D. Modolo, and V. Ferrari. "Do semantic parts emerge in convolutional neural networks?", arXiv preprint arXiv:1607.03738, pp. 1-18, 2016.

Soheil Kolouri, Charles E Martin, and Heiko Hoffmann. "Explaining Distributed Neural Activations via Unsupervised Learning" by Conference on Computer Vision and Pattern Recognition, Explainable Computer Vision Workshop, pp. 1670-1678, 2017.

J. Salamon, C. Jacoby and J. P. Bello, "A Dataset and Taxonomy for Urban Sound Research", 22nd ACM International Conference on Multimedia, Orlando USA, Nov. 2014, pp. 1-4.

Kolouri, S., Tosun, A.B., Ozolek, J.A. and Rohde, G.K., 2016. A continuous linear optimal transport approach for pattern analysis in image datasets. Pattern recognition, 51, pp. 453-462.

Berisha, V., Liss, J., Sandoval, S., Utianski, R. and Spanias, A., May 2014. Modeling pathological speech perception from data with similarity labels. In Acoustics, Speech and Signal Processing (ICASSP), 2014 IEEE International Conference on, IEEE, pp. 915-919.

Bordes, A., Usunier, N., Garcia-Duran, A., Weston, J. and Yakhnenko, O., 2013. Translating embeddings for modeling multi-relational data. In Advances in neural information processing systems, pp. 2787-2795.

Chen, T., Tang, L.A., Sun, Y., Chen, Z. and Zhang, K., 2016. Entity embedding-based anomaly detection for heterogeneous categorical events. arXiv preprint arXiv:1608.07502, pp. 1-8.

Chen, T. and Sun, Y., Feb. 2017. Task-Guided and Path-Augmented Heterogeneous Network Embedding for Author Identification. In Proceedings of the Tenth ACM International Conference on Web Search and Data Mining, pp. 295-304, ACM.

He, K., Zhang, X., Ren, S. and Sun, J., 2016. Deep residual learning for image recognition. In Proceedings of the IEEE Conference on Computer Vision and Pattern Recognition, pp. 770-778.

Jiao, Y., Berisha, V., Liss, J., Hsu, S.C., Levy, E. and McAuliffe, M., 2017. Articulation entropy: An unsupervised measure of articulatory precision. IEEE Signal Processing Letters, 24(4), pp. 485-489.

Rafiqi, S., Wangwiwattana, C., Kim, J., Fernandez, E., Nair, S. and Larson, E.C., Jul. 2015. PupilWare: towards pervasive cognitive load measurement using commodity devices. In Proceedings of the 8th ACM International Conference on PErvasive Technologies Related to Assistive Environments, p. 42, ACM.

Tang, J., Qu, M., Wang, M., Zhang, M., Yan, J. and Mei, Q., May 2015. Line: Large-scale information network embedding. In Proceedings of the 24th International Conference on World Wide Web, pp. 1067-1077, ACM.

Tryon, W.W., 1975. Pupillometry: A survey of sources of variation. Psychophysiology, 12(1), pp. 90-93.

Wang, J., Fan, Y., Zhao, X. and Chen, N., 2014. Pupillometry in Chinese female patients with depression: a pilot study. International journal of environmental research and public health, 11(2), pp. 2236-2243.

Wisler, A., Berisha, V., Liss, J. and Spanias, A., Dec. 2014. Domain invariant speech features using a new divergence measure. In Spoken Language Technology Workshop (SLT), 2014 IEEE, pp. 77-82.

Xie, J., Girshick, R. and Farhadi, A., 2016. Unsupervised deep embedding for clustering analysis. In International Conference on Machine Learning (ICML), pp. 1-10.

Zhou, B., Khosla, A., Lapedriza, A., Oliva, A. and Torralba, A., 2016. Learning deep features for discriminative localization. In Proceedings of the IEEE Conference on Computer Vision and Pattern Recognition, pp. 2921-2929.

Berisha, V., Kwon, H. and Spanias, A., Jul. 2006. Real-time implementation of a distributed voice activity detector. In Sensor Array and Multichannel Processing, 2006. Fourth IEEE Workshop on, IEEE, pp. 659-662.

Lu, X., Tsao, Y., Matsuda, S. and Hori, C., Aug. 2013. Speech enhancement based on deep denoising autoencoder. In Interspeech, pp. 436-440.

Tranter, S.E. and Reynolds, D.A., 2006. An overview of automatic speaker diarization systems. IEEE Transactions on audio, speech, and language processing, 14(5), pp. 1557-1565.

Berisha, V., Sandoval, S., Utianski, R., Liss, J. and Spanias, A., May 2013. Selecting disorder specific features for speech pathology fingerprinting. In Acoustics, Speech and Signal Processing (ICASSP), 2013 IEEE International Conference on, IEEE, pp. 7562-7566.

Sotiras, A., Resnick, S. M. and Davatzikos, C., "Finding imaging patterns of structural covariance via non-negative matrix factorization." NeuroImage 108 (2015): pp. 1-16.

Simonyan, K. and Zisserman, A., "Very deep convolutional networks for large-scale image recognition." arXiv preprint arXiv:1409.1556(2014), pp. 1-14.

Activity Recognition system based on Multisensor data fusion (AReM) Data Set, UCI Machine Learning Repository, found at https ://archive .ics.uci. edu /ml/datasets /Activity+ Recognition +system+based +on+ Multisensor+data+fusion +(AReM), taken on Jan. 31, 2019.

A. Harshman in "Foundations of the PARAFAC procedure: Model and conditions for an explanatory multi-mode factor analysis," UCLA Working Papers in Phonetics, vol. 16, 1970, pp. 1-84.

Tomasi in Practical and computational aspects in chemometric data analysis, Ph.D. thesis, Department of Food Science, The Royal Veterinary and Agricultural University, Frederiksberg, Denmark, 2006, pp. 1-286.

(56) References Cited

OTHER PUBLICATIONS

N. Sidiropoulos et al. in "Tensor decomposition for signal processing and machine learning," IEEE Trans. on Signal Processing, vol. 65, No. 13, 2017, pp. 3551-3582.

* cited by examiner

SYSTEM AND METHOD FOR HEALTH ASSESSMENT ON SMARTPHONES

CROSS-REFERENCE TO RELATED APPLICATIONS

The present application is a Continuation-in-Part application of U.S. application Ser. No. 16/034,780, filed on Jul. 13, 2018, which is a non-provisional patent application of U.S. Provisional Application No. 62/558,094, filed Sep. 13, 2017, the entirety of which are hereby incorporated by reference.

The present application is ALSO a Continuation-in-Part application of U.S. application Ser. No. 16/118,161, filed on Aug. 30, 2018, which is a non-provisional patent application of U.S. Provisional Application No. 62/581,625, filed on Nov. 3, 2017, the entirety of which are hereby incorporated by reference.

The present application ALSO claims the benefit of and is a non-provisional patent application of U.S. Provisional Application No. 62/627,123, filed on Feb. 6, 2018, the entirety of which is hereby incorporated by reference.

BACKGROUND OF INVENTION

(1) Field of Invention

The present invention relates to a health assessment system and, more specifically, to a system and method that passively and opportunistically captures data from smartphones for physical health assessment.

(2) Description of Related Art

Health management and assessment is important for a variety of purposes. Determining the health status of individuals in various occupations is currently achieved through periodic assessments performed in-person by medical professionals and relies heavily on self-selection and self-reporting. Resource-intensive, intrusive, and relatively infrequent, this approach is sub-optimal for determining health status of human subjects over a target period of time. Attempts to leverage the massive base of smartphones to obtain rich sensor data for disease diagnosis have had limited success. Many of the algorithms designed to provide diagnostics using signal data require specialized recordings of physiological measures in a laboratory environment, such as diagnostic algorithms detecting heart abnormalities in a database of electrocardiography (ECG) data. Generalized recordings from standard commodity smartphone sensors would not work in this context. Many approaches attempt to tap into the processing power of smartphones, but rely on additional sensors in order to achieve their diagnostic power, or simply use the smartphone as a convenient terminal to upload to a centralized database. The former solution is not scalable because it requires supplying external devices to the patient pool, raising costs and potentially impacting compliance in large occupational populations. The latter solution is limited in that it does not leverage sensor-based health monitoring.

Thus, a continuing need exists for a health assessment system that does not require specialized diagnostic equipment to be worn by the individual, but instead, is able to employ commodity smartphones already possessed by the vast majority of the population.

SUMMARY OF INVENTION

This disclosure provides a system for health assessment. In various aspect, the system includes a mobile device having at least one of an accelerometer, a geographic location sensor, and a camera. The mobile device includes at least one or more processors and a memory, the memory being a non-transitory computer-readable medium having executable instructions encoded thereon, such that upon execution of the instructions, the one or more processors perform several operations. For example, the system obtains sensor data related to an operator of the mobile device from one of the sensors. A network of networks (NoN) is generated based on the sensor data, the NoN having a plurality of layers with linked nodes. Tuples are thereafter generated. Each tuple contains a node from each layer that optimizes importance, diversity, and coherence. Storylines are created based on the tuples that solve a longest path problem for each tuple. The storylines tracks multiple symptom progressions of the operator. Finally, a disease prediction of the operator is provided based on the storylines.

In another aspect, the plurality of layers includes a context layer, a predictor layer, and an activity layer. The context layer represents features within the sensor data, the activity layer represents detected activities of the operator based on the sensor data, and the predictor layer represents domain knowledge regarding at least one disease.

In yet another aspect, each node within the context layer is a feature value of the operator. Further, pairs of nodes are linked according to their similarity such that a link between feature nodes indicates that feature measurements corresponds to the operator taken at a common time stamp.

In another aspect, each node within the activity layer is an activity classification of the operator, and pairs of nodes are linked according to their similarity such that a link between activity nodes indicates that activity classification corresponds to the operator taken at a common time stamp.

Additionally, each node within the predictor layer is a disease classification based on domain knowledge.

In another aspect, the storylines are temporal motifs. Each temporal motif is a subgraph of the NoN that comprises nodes that are linked across different tuples and nodes that are linked across a temporal dimension.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
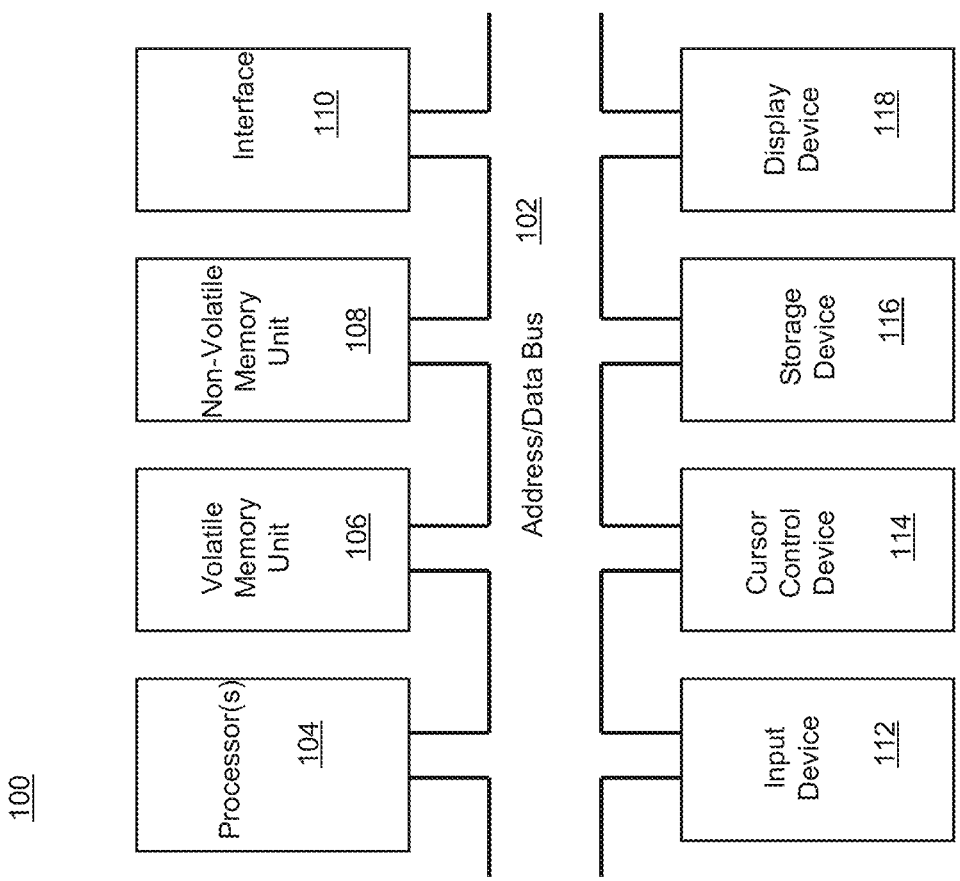
FIG. 1 is a block diagram depicting the components of a system according to various embodiments of the present invention.

The present invention relates to a health assessment system and, more specifically, to system and method that passively and opportunistically captures data from smartphones for physical health assessment. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Kolouri, S., Tosun, A. B., Ozolek, J. A. and Rohde, G. K., 2016. A continuous linear optimal transport approach for pattern analysis in image datasets. Pattern recognition, 51, pp. 453-462.
2. Berisha, V., Liss, J., Sandoval, S., Utianski, R. and Spanias, A., 2014, May. Modeling pathological speech perception from data with similarity labels. In Acoustics, Speech and Signal Processing (ICASSP), 2014 IEEE International Conference on (pp. 915-919). IEEE.
3. Bordes, A., Usunier, N., Garcia-Duran, A., Weston, J. and Yakhnenko, O., 2013. Translating embeddings for modeling multi-relational data. In *Advances in neural information processing systems* (pp. 2787-2795).
4. Chen, T., Tang, L. A., Sun, Y., Chen, Z. and Zhang, K., 2016. Entity embedding-based anomaly detection for heterogeneous categorical events. *arXiv preprint arXiv:* 1608.07502.
5. Chen, T. and Sun, Y., 2017, February. Task-Guided and Path-Augmented Heterogeneous Network Embedding for Author Identification. In *Proceedings of the Tenth ACM International Conference on Web Search and Data Mining* (pp. 295-304). ACM.
6. He, K., Zhang, X., Ren, S. and Sun, J., 2016. Deep residual learning for image recognition. In Proceedings of the IEEE Conference on Computer Vision and Pattern Recognition (pp. 770-778).
7. Jiao, Y., Berisha, V., Liss, J., Hsu, S. C., Levy, E. and McAuliffe, M., 2017. Articulation entropy: An unsupervised measure of articulatory precision. IEEE Signal Processing Letters, 24(4), pp. 485-489.
8. Rafiqi, S., Wangwiwattana, C., Kim, J., Fernandez, E., Nair, S. and Larson, E. C., 2015, July. PupilWare: towards pervasive cognitive load measurement using commodity devices. In Proceedings of the 8th ACM 9. Tang, J., Qu, M., Wang, M., Zhang, M., Yan, J. and Mei, Q., 2015, May. Line: Large-scale information network embedding. In Proceedings of the 24th International Conference on World Wide Web (pp. 1067-1077). ACM.
10. Tryon, W. W., 1975. Pupillometry: A survey of sources of variation. Psychophysiology, 12(1), pp. 90-93.
11. Wang, J., Fan, Y., Zhao, X. and Chen, N., 2014. Pupillometry in Chinese female patients with depression: a pilot study. International journal of environmental research and public health, 11(2), pp. 2236-2243.
12. Wisler, A., Berisha, V., Liss, J. and Spanias, A., 2014, December. Domain invariant speech features using a new divergence measure. In Spoken Language Technology Workshop (SLT), 2014 IEEE (pp. 77-82). IEEE.
13. Xie, J., Girshick, R. and Farhadi, A., 2016. Unsupervised deep embedding for clustering analysis. In International Conference on Machine Learning (ICML).
14. Zhou, B., Khosla, A., Lapedriza, A., Oliva, A. and Torralba, A., 2016. Learning deep features for discriminative localization. In Proceedings of the IEEE Conference on Computer Vision and Pattern Recognition (pp. 2921-2929).
15. Berisha, V., Kwon, H. and Spanias, A., 2006, July. Real-time implementation of a distributed voice activity detector. In Sensor Array and Multichannel Processing, 2006. Fourth IEEE Workshop on (pp. 659-662). IEEE.
16. Lu, X., Tsao, Y., Matsuda, S. and Hori, C., 2013, August. Speech enhancement based on deep denoising autoencoder. In Interspeech (pp. 436-440).
17. Tranter, S. E. and Reynolds, D. A., 2006. An overview of automatic speaker diarization systems. IEEE Transactions on audio, speech, and language processing, 14(5), pp. 1557-1565.
18. Berisha, V., Sandoval, S., Utianski, R., Liss, J. and Spanias, A., 2013, May. Selecting disorder specific features for speech pathology fingerprinting. In Acoustics, Speech and Signal Processing (ICASSP), 2013 IEEE International Conference on (pp. 7562-7566). IEEE.
19. Sotiras, A., Resnick, S. M. and Davatzikos, C., "Finding imaging patterns of structural covariance via non-negative matrix factorization." *NeuroImage* 108 (2015): 1-16.
20. Simonyan, K. and Zisserman, A., "Very deep convolutional networks for large-scale image recognition." *arXiv preprint arXiv:* 1409.1556(2014).
21. Activity Recognition system based on Multisensor data fusion (AReM) Data Set, UCI Machine Learning Repository, found at https://archive .ics.uci.edu/ml/datasets/Activity+Recognition+system+based+on+Multisensor+data+fusion+(AReM), taken on Jan. 31, 2019.

(2) Principal Aspects

Various embodiments of the invention include three "principal" aspects. The first is a system for health assessment. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
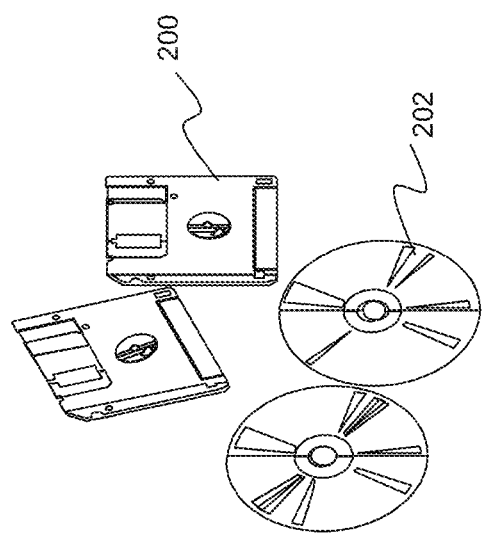
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

This disclosure provides a unique system that passively and opportunistically captures data from smartphones for robust, multi-modal, temporally-sensitive evaluation and assessment of health. Appraising and analyzing occupational preparedness is a specific application for health assessment. The system of the present disclosure, referred to as Somatic Opportunistic Mobile Assessment Technologies Implemented on Cellphones (SOMATIC), is comprised of signal reconstruction software powered by Independent Component Analysis of Tensors (ICAT), automated activity and context classification using Deep Sense Learning (DSL), and advanced disease detection methods and analytics modules for gaze tracking, speech/cough analysis, and gait/motor tracking. Binding the entire system together, a network-of-networks (NoN)-based summarization technology evaluates disease classification based on the multiple hypotheses and biomarkers produced by the underlying system and leverages the framework to produce salient disease progression profiles to aid diagnosis and prediction. Using a combination of technologies described below, SOMATIC addresses remote health and readiness monitoring by utilizing qualitatively variable, yet quantitatively ubiquitous sensing technology in scalable fashion to determine disease and impairment states of users through multimodal and temporal analysis of activities, contexts, and biomarkers.

A purpose of the system is to continuously assess the health and readiness of individuals using smartphones. Unlike the current state of the art, the present system does not require specialized diagnostic equipment to be worn by the individual; instead, the system described herein is able to employ commodity smartphones already possessed by the vast majority of the population. Opportunistic health monitoring and diagnostics on mobile devices is a significant technology that provides for a lot of applications. In the defense sector this technology offers the capability of on-the-field evaluation and diagnostics of warfighter physical health and preparedness. In consumer health monitoring, the invention of this disclosure can be used to extend the current generation of devices (Fitbit, etc.) to the next generation of devices for health analytics and diagnostics. In the automotive industry, these technologies could detect driver drowsiness, neurological impairment (alcohol, drugs, etc.), distraction, or a health emergency. In the manufacturing sector, these technologies could also be used for enhancing worker safety by alerting supervisors of worker impairment, as well as providing injury prediction. Further details regarding the present system are provided below.

(4) Specific Details of Various Embodiments

Figure 3:
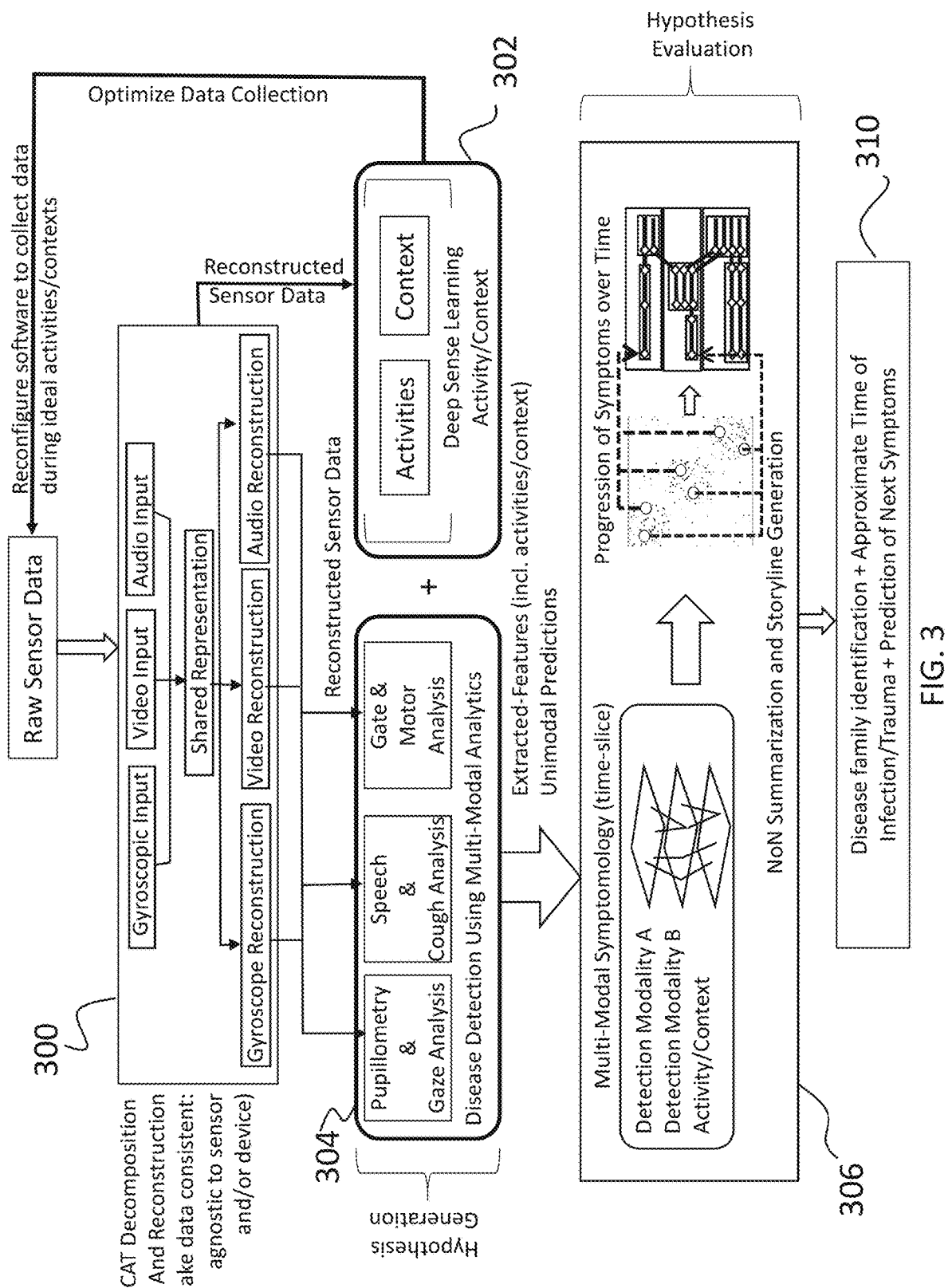
FIG. 3 is a flowchart depicting a method for health assessment according to various aspects of the present invention.

As noted above, the present disclosure is directed to a system for health assessment of smartphone users in a variety of environments. As shown in FIG. 3, the system includes a collection of health data analytics components that include: (1) ICAT-based Sensor Fusion/Reconstruction 300 (as described in U.S. patent application Ser. No. 16/034,780 (which is incorporated herein by reference)), which includes tensor decomposition techniques to reconstruct incomplete and erroneous information leveraging simultaneous, alternate data streams; (2) DSL-based Activity and Context Recognition 302 (as described in U.S. patent application Ser. No. 16/118,161 (which is incorporated herein by reference)), which provides unsupervised activity and context classification based on the automated identification of salient subcomponents of activity/context taxonomies; (3) multi-modal health outcome predictors 304 to identify biomarkers of Traumatic Brain Injury (TBI) and infectious diseases; and (4) NoN Summarization 306 (as described in U.S. patent application Ser. No. 16/033,178 (which is incorporated herein by reference)), which includes temporally-sensitive motif generators operating across multimodal network layers to assess disease susceptibility and progression. This system is driven entirely by passive, opportunistic mobile sensing across a diverse, unstandardized set of devices and individuals to provide a disease diagnosis 310 result. This summarization of the vast feature and symptom space of the detection modalities provides accurate disease family identification as well as probable onset of disease symptoms/biomarker-correlates.

Figure 4:
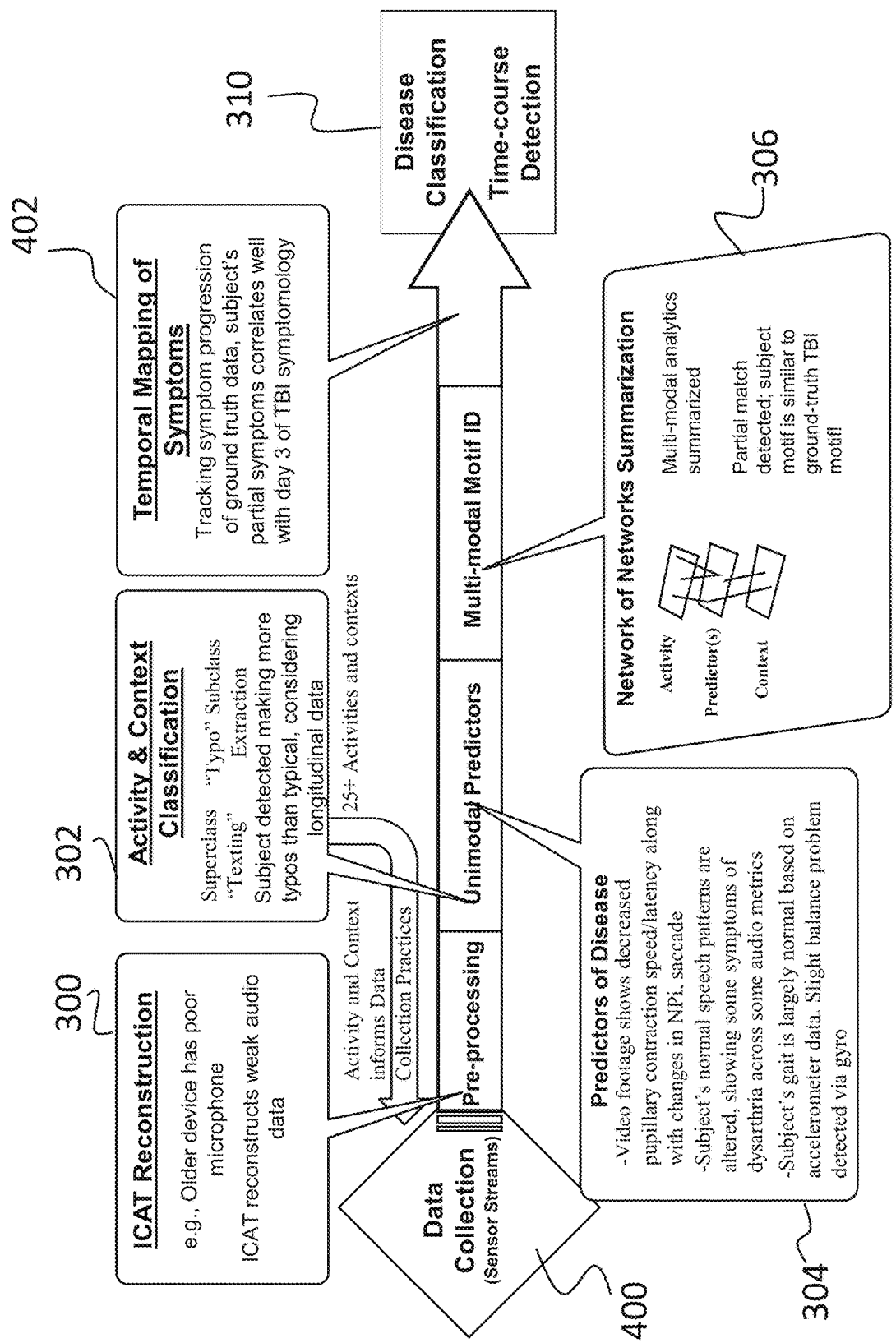
FIG. 4 is a flowchart depicting a system for health assessment according to various aspects of the present invention.

As shown in FIG. 4, the process begins with smartphone data sources 400 that are likely to be inconsistent, noisy, incomplete, and weak. Sensor fusion and reconstruction using ICA of tensors leveraging multi-modal data is used to produce higher-quality source signals for analysis. The unique ICAT method 300 can perform this computation with minimal overhead, and is a scalable solution for very large subject pool sizes and continually recorded datasets. Next, using Deep Sense Learning (DSL) 302, the system can build an activity and context database automatically based on salience, thereby improving the breadth and accuracy of the classifier. The classification accuracy is increased, even given few examples (subcomponents are considered critical features of superclass definitions and boost classification sample size) and DSL expands the taxonomy of potential activities and contexts automatically.

Given user activity and context, the system proceeds to opportunistically deploy the disease detection modalities 304. For example, in the case that the user is facing his/her smartphone, the front facing camera provides pupillometry, which enables diagnosis of even subtle changes after acute or chronic TBI. In the case that the user is speaking into the microphone, voice quality processing algorithms yield rich feature sets describing speech articulation quality and provide entropy measures indicating deviation from norms. If the user is walking, gait analysis algorithms detect subtle features in gait and motor control to identify markers of motor and balance dysfunction.

Finally, because some of the aforementioned analyses may be inconclusive, the system employs multiple modalities to provide an accurate result. Using NoN-based summarization 306, the system incorporates many different modalities of disease progression and uses them in combination to determine co-morbidity, interaction effects, and best-hypothesis selection. In some aspects, the system can proceed to provide temporal mapping of systems 402, where previously mapped, ground-truth symptomology (e.g., of TBI) enable the identification of the suspected disease state to a disease (e.g., a TBI) timeline. For example, the suspected case of TBI most closely resembles TBI symptom progression at Day 3 following injury. The result is an accurate disease diagnosis 310, including information about the approximate progression of the disease. Further details regarding each of these components are provided below.

(4.1) Sensor Fusion and Reconstruction Using ICA of Tensors (ICAT) Component A fundamental challenge in processing smartphone sensor streams is the establishment of context for signals, extraction of weak relevant signals from interference, and filling in gaps in relevant signals. The challenge is typically met using a form of tensor decomposition, but these techniques are difficult to implement in the context of the concept of operations herein, as the scale and exigency requirements of the analytics require algorithms to be fast and computationally efficient. Traditional non-linear least squares (NLS) algorithms are neither.

The system of this disclosure uses a sensor fusion framework based on modeling the relationships between sensor activity signatures and different contexts using a tensor representation. The tensor is analyzed using a unique Independent Component Analysis of Tensors (ICAT) tensor decomposition method as described in U.S. patent application Ser. No. 16/034,780 (which is incorporated by reference as though fully set forth herein). The present system uses the dimensions or modes of the tensor to represent both sensor data and contextual conditions such as time-of-day, geographic location, signals from other individuals, etc. The tensor element values represent the relationships between signals and contexts. Tensor decomposition can then reveal hidden structure in the relationships which can be used to extract weak signals and predict or fill-in missing sensor data.

Tensor decomposition has been used successfully in many applications involving multi-dimensional data, sensor fusion applications, chemometrics, and social network activity analysis. For example, it was verified in pilot studies that ICAT speeds up tensor composition by greater than 50×, scales linearly with tensor order instead of exponentially, and is more accurate for sub-sampled and sparse data compared to state-of-the-art methods. This makes ICAT ideal for real-time context-based processing of noisy and incomplete signals from smartphone sensors.

Figure 5:
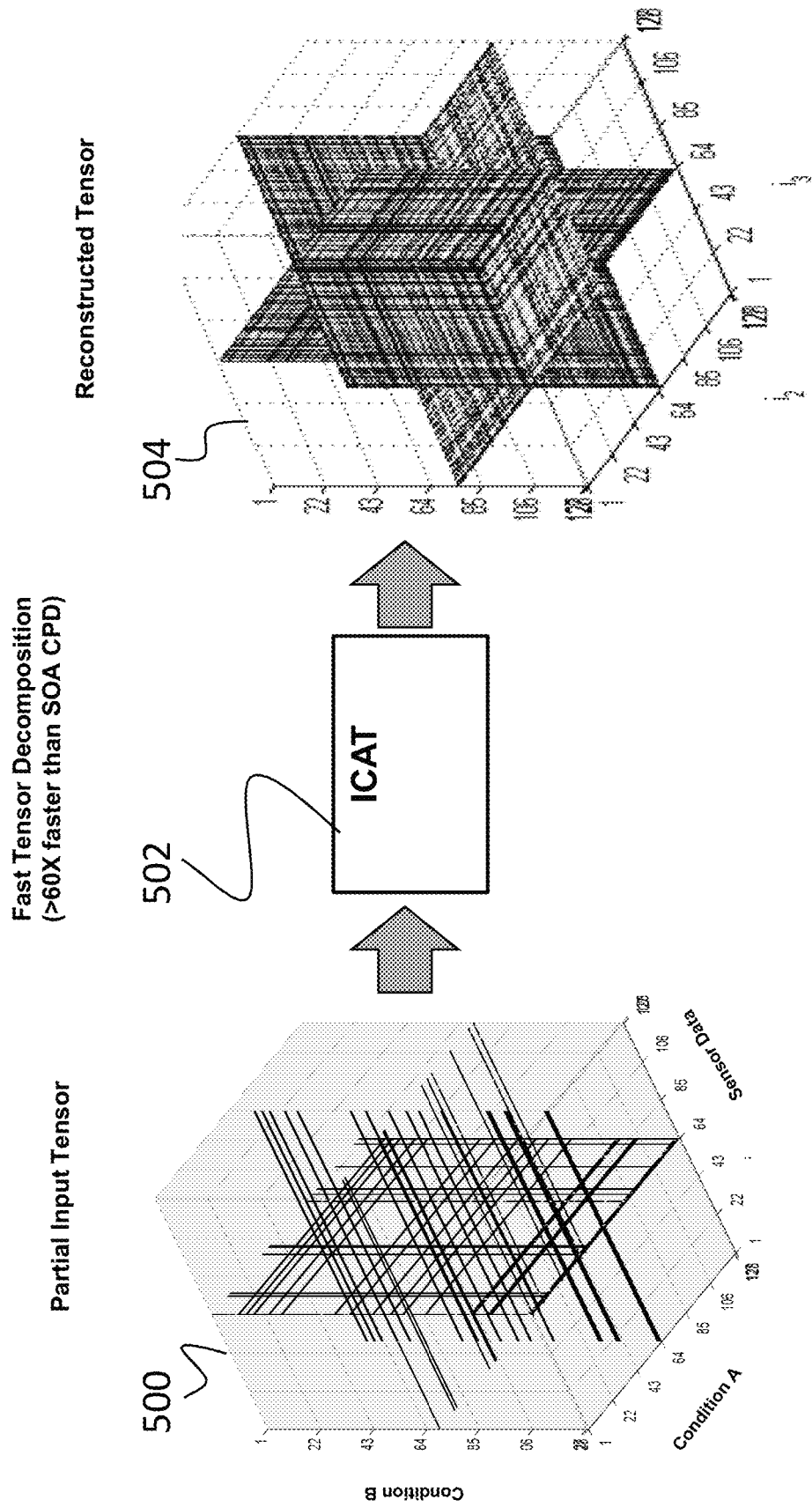
FIG. 5 is an illustration depicting the reconstruction of context-based sensor data and extraction of walking and cycling signals according to various aspects of the present invention.

FIG. 5, for example, depicts an example of ICAT employed to reconstruct and extract walking and cycling signals from noisy, context-based sensor data using the AReM (Activity Recognition System based on Multisensor data fusion) human activity dataset (see Literature Reference No. 21) collected using RF sensors worn by human subjects. The image depicts a partial input tensor 500 (various slices of 3D subsampled input), fast tensor decomposition 502, resulting in a reconstructed tensor 504. The partial input tensor 500 includes partial data consisting of tensor slices (mixtures) of signals collected under various conditions. Various combinations of conditions define different contexts for sensor processing.

Figure 6:
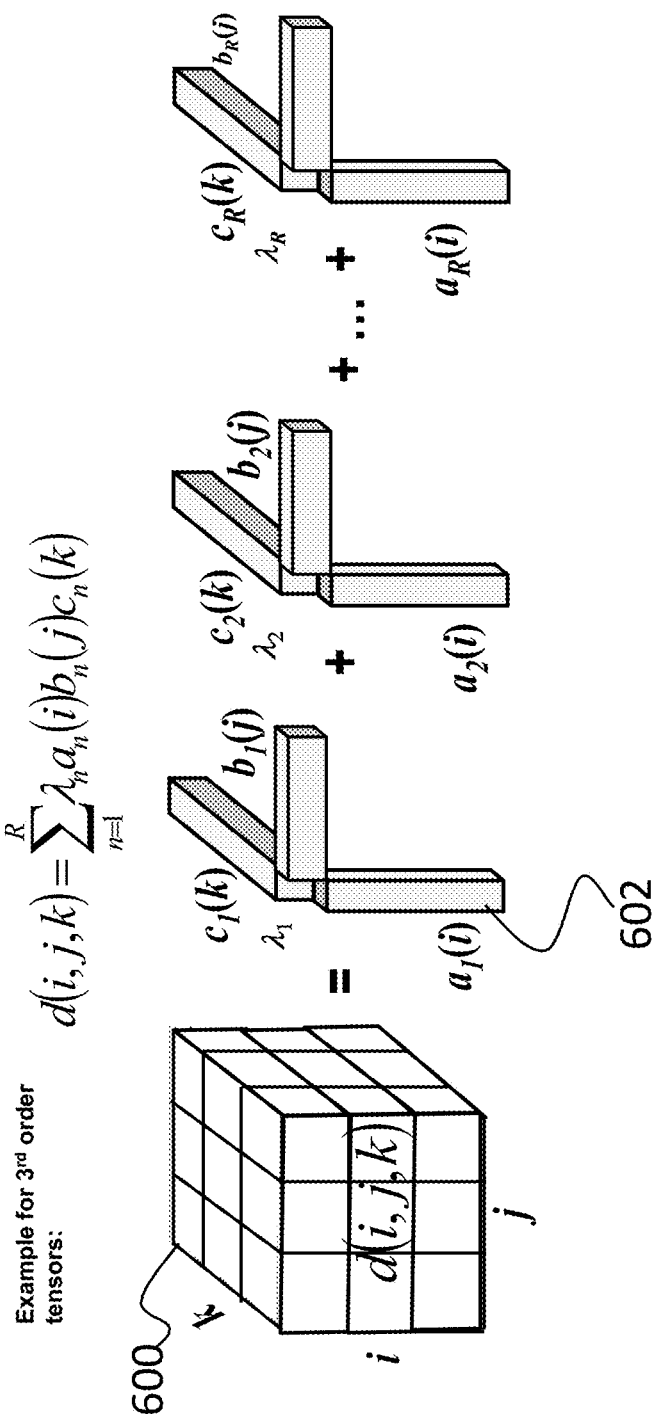
FIG. 6 is an illustration depicting how canonical polyadic decomposition (CPD) of tensors into factors reveals tensor structure, which the system uses for denoising, data completion, and health signature extraction according to various aspects of the present invention.

ICAT is based on the canonical polyadic decomposition (CPD) form of tensor decomposition, as shown in FIG. 6. CPD of tensors 600 into factors 602 reveals structure in tenors which ICAT uses for denoising, data completion, and health signature extraction. In analogy to singular value decomposition (SVD) of matrices, CPD decomposes a tensor into a weighted sum of R tensor factors, each of which is given by an outer product of D tensor mode factors or vectors where D is the tensor order and R is the rank of the tensor. A smaller R indicates more structure in the data since the CPD representation has only RDN parameters compared to $N^D$ parameters for a D-order tensor with N elements per mode. If some mild conditions on the tensor are met, the decomposition is guaranteed to be unique, which is not the case for matrix decompositions. Therefore, if one were to use different methods to decompose the tensor and the resulting reconstruction errors are low, then the decompositions will be the same.

Figure 7:
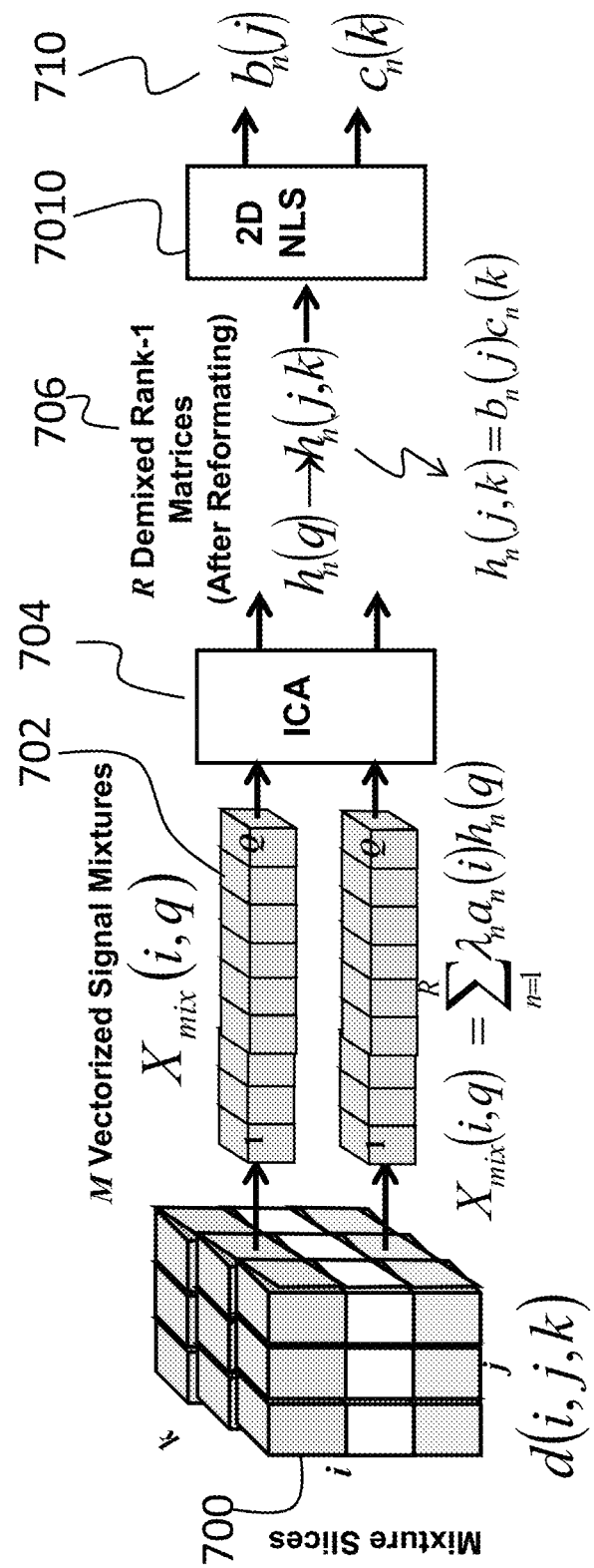
FIG. 7 is an illustration depicting a first step of a method for health assessment according to various aspects of the present invention.
Figure 8:
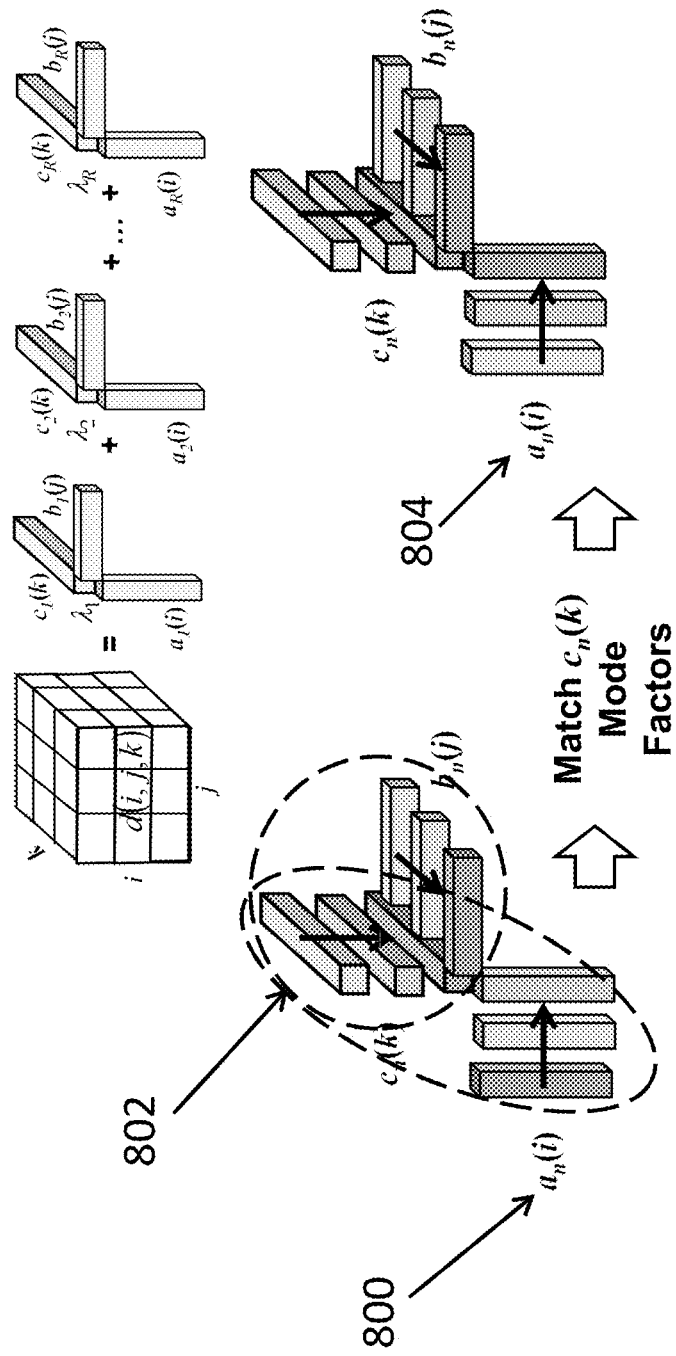
FIG. 8 is an illustration depicting a second step of the method for health assessment according to various aspects of the present invention.

Unlike the state-of-the-art methods, ICAT uses statistical independence to decompose tensors. An example is shown in FIGS. 7 and 8 using a tensor with three modes. First, 2D horizontal slices 700 in the second and third modes of the tensor are converted into 1D vectors 702 and used as signal mixtures for input to Independent Component Analysis (ICA) 704. Each of the R demixed outputs 706 of ICA 704 are then converted 7010 back to a 2D slice format. The n-th output of ICA is then a rank-1 matrix 710 that is the outer-product of the factors for tensor mode n. A conventional least-squares algorithm such as non-linear least squares NLS is used to separate each rank-1 output matrix into factors for the second and third modes ($b_n$ and $c_n$). These two mode factors are automatically correctly assigned to tensor factors as parts of the same demixing operation. The system determines the first (an) and third mode factors by using vertical slices of the tensor as mixture inputs to ICA. Repeated for clarity, FIG. 7 depicts a first step of the ICAT algorithm, which extracts the tensor mode factors. Horizontal slices 700 of the tensor are vectorized and used as mixture inputs to ICA 704. The ICA outputs are processed using NLS to determine the $b_n(j)$ and $c_n(k)$ mode factors. This flow is repeated using vertical mixture slices to extract the $a_n(i)$ and $c_n(k)$ mode factors. However, since the ordering of ICA outputs is indeterminate and the factors for the first mode were determined in a different demixing operation, the system still needs to assign the demixed first mode factors to the correct tensor factor.

The system implements the method shown in FIG. 8 to assign the $a_n$ mode factors to the correct tensor factors. Initially 800, the $a_n$ mode factors are not assigned to the correct tensor modes because they were demixed separately from $b_n$ and $c_n$. Alternatively, the $b_n$ and $c_n$ mode factors 802 are correctly matched because they were demixed together. The solution is to use the common $c_n$ mode factors 804 to find the correct an mode assignments. The system searches for the best matches of $c_n$ between the two demixings separately for each of the R tensor mode factors, which requires only a linearly scaling set of vector matching operations, rather than an exponential one, resulting in a huge reduction in computational complexity for high rank tensors. Once the correct mode factor assignments have been determined, the tensor weight factors $\lambda_n$ are calculated by setting up a system of linear equations using a subset of the measured tensor values and solving for $\lambda_n$. This algorithm is easily generalizable to tensors of arbitrary order. Thus, Step 2 of ICAT algorithm as depicted in FIG. 8 resolves ICA permutation ambiguity, assigns mode factors to correct tensor factors, and calculates tensor factor weights $\lambda_n$.

Figure 9:
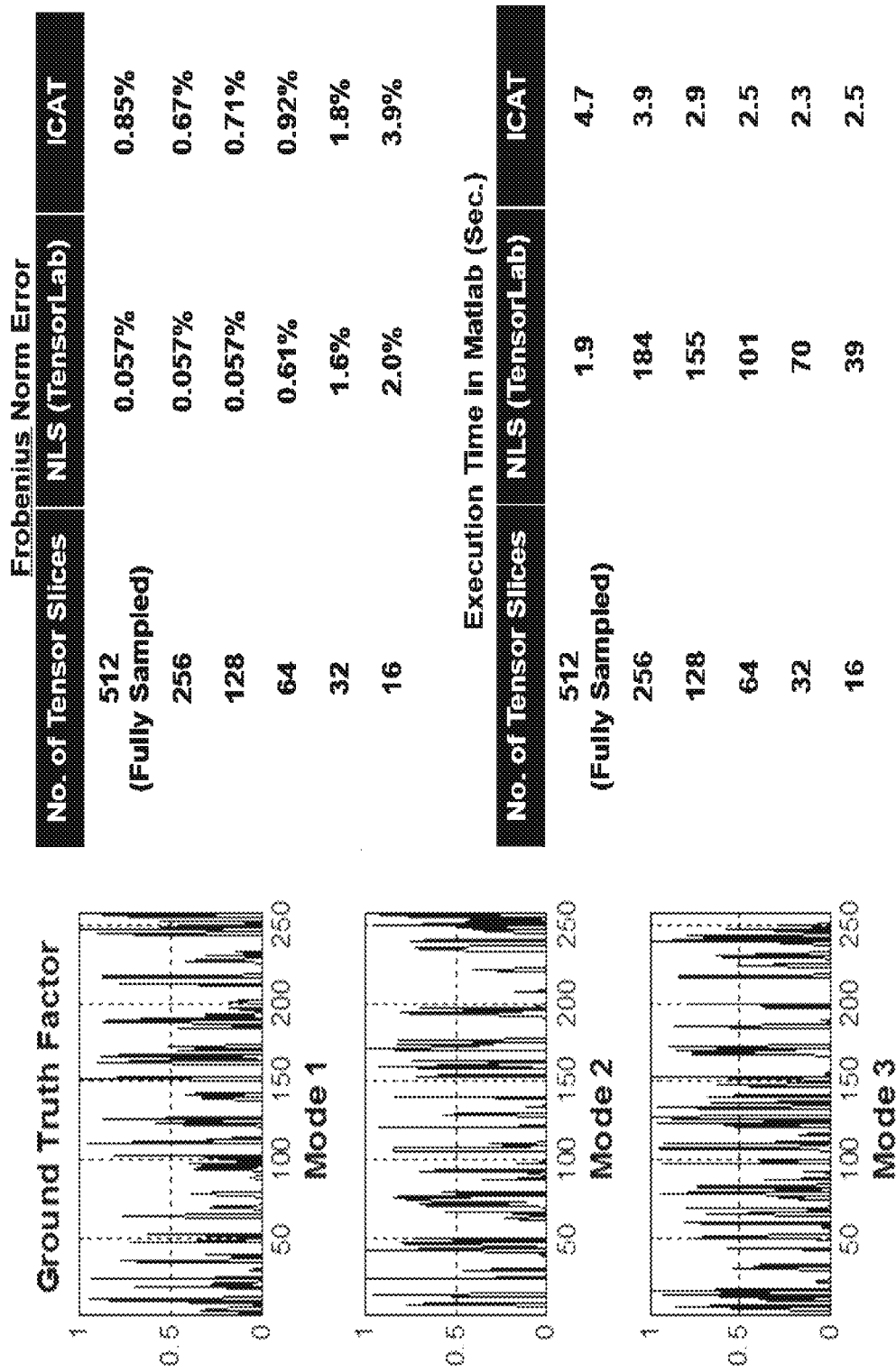
FIG. 9 is an illustration depicting a comparison of results provided by a prior art system and a system according to principles of the present invention.

The effectiveness of the ICAT algorithm was demonstrated in pilot studies and the results are summarized in FIGS. 5 and 9. In FIG. 5, it is shown that results for ICAT extraction of relevant signals from interference using a data set allowed the system to reconstruct the tensor with 89% of the tensor missing; and walking and cycling signals were extracted from the interference with 0.33% error. The Matlab execution time was 1.7 sec. This can be compared with the 0.28% reconstruction error and 105 sec execution time of the state of the art NLS algorithm implemented in TensorLab.

FIG. 9 compares the tensor reconstruction error and execution time of ICAT and NLS. The 256×256×256 tensor used as input data was generated synthetically using mode factors consisting of peaks with random values, widths, and separations. The tensor reconstruction error was expressed in terms of the Frobenius norm (an extension of rms error to tensors). It is clear that for data that is even slightly subsampled, ICAT had a big speed advantage over NLS ranging from 47× to 16× while still having low reconstruction errors. NLS had an accuracy advantage for higher sampling rates, but the advantage disappeared when the data sampling was sufficiently sparse. A small amount of noise needed to be added to the data for NLS to converge. ICAT performed well with or without the added noise.

(4.2) Deep Sense Learning (DSL) Component for Activity Recognition

Given that human activity varies widely between subjects and even within a single task, it is challenging to pick up meaningful signals in biometric data for disease analysis in the presence of this variability. There is a need for fine-grained activity analysis and a dissection of activities into components. An additional challenge is to avoid labeling each component, which would be too time consuming and costly. Instead, unsupervised methods are required to extract such components automatically.

The system of the present disclosure specifies an unsupervised learning method that can automatically identify key components of an activity from inertial sensor data, enabling improved activity recognition and additional detail and context for disease analysis. The approach reduces errors in recognition by 80% compared to deep learning alone and autonomously dissects activities into their components, providing additional inputs for improved disease recognition. The unsupervised method of the present disclosure reuses a pre-trained convolutional neural network (CNN) and analyzes the distributed activation patterns of this network. To extract components from the input, a saliency measure is used based on the responses of the pre-trained CNN and salient time segments are extracted. The corresponding patterns of neural activations for the extracted salient regions are then clustered with an unsupervised method. The resulting cluster centers correspond to key components of human activities.

Figure 10:
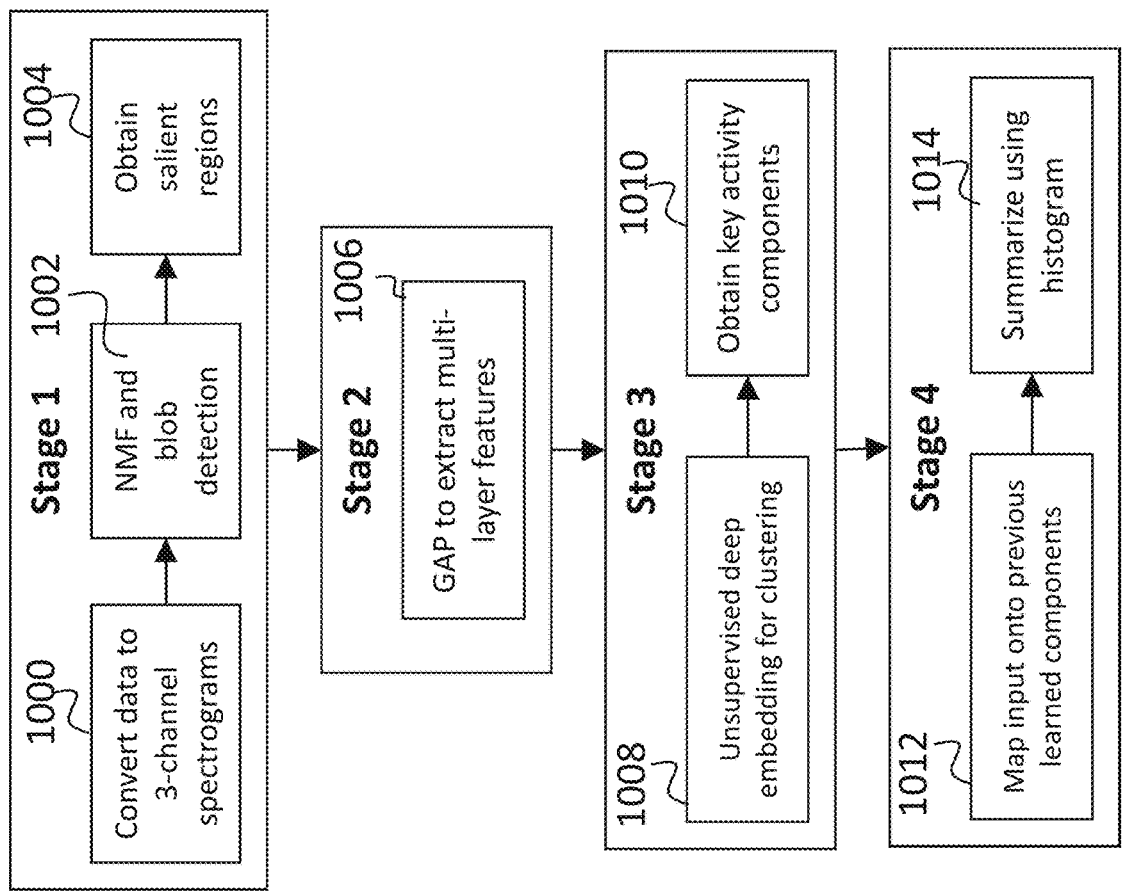
FIG. 10 is a flow chart illustrating a method for deep sense learning according to various aspects of the present invention.

The DSL component includes four main stages (see FIG. 10). In stage one, a top-down approach is utilized to pinpoint the salient parts of the input data based on the network activation patterns. Initially, the input data is converted to spectrograms with three channels 1000. For example, accelerometer data is converted into spectrograms with three channels, one each for the, y, and z directions (analogue to the RGB colors in an image). Then, elastic non-negative matrix factorization (NMF) 1002 is used together with an off-the-shelf blob detector to obtain multi-scale salient regions 1004 of the spectrogram images. The NMF components of activation provide localized, tightly clustered, and blob-like regions that correspond to different semantic components of the input data.

In stage two, a bottom-up approach probes a convolutional neural network (CNN) and extracts hierarchical responses of the network, throughout all layers. More precisely, the system carries out global average pooling (GAP) (see Literature Reference Nos. 6 and 14) at different convolutional layers of the network and extracts fixed size multi-layer features 1006. These extracted GAP features represent various patterns of activations in the network.

In the third stage, an iterative unsupervised learning approach is applied to the GAP features to identify the key activity components learned by the network. To cluster the GAP features, unsupervised deep embedding for clustering 1008 (see Literature Reference No. 13) is used. The cluster centers then become the key components 1010. The DSL method can extract key components in an unsupervised way. The components are semantically meaningful, e.g., clusters of wheels and legs. The unsupervised approach of the present disclosure addresses the challenge of unlabeled data.

More precisely, let $X=[x_k]_{k=1}^{m} \in R^{d \times m}$ denote the vectorized CNN responses of the last convolutional layer (e.g. the 'conv5_4' of VGG19 (see Literature Reference No. 20), where m is the number of convolutional kernels at the last layer (e.g. m=512 in VGG19), and d is the number of nodes per convolutional kernel and scales with the size of the input image. Then the NMF is formulated as, $$\operatorname{argmin}_{W,H} \frac{1}{2}\|X - HW\|_F^2 + \gamma\lambda(\|W\|_1 + \|H\|_1) + \frac{1}{2}\gamma(1-\lambda)(\|W\|_F^2 + \|H\|_F^2)$$

where $\|\cdot\|_F$ is the Frobenius norm, $\|\cdot\|_1$ is the elementwise $L_1$ norm, columns of $H \in R^{d \times r}$ are the non-negative components, $W \in R^{r \times m}$ is the non-negative coefficient matrix, r is the rank of matrix H, which corresponds to the number of extracted components, and $\lambda$ and $\gamma$ are regularization parameters. A coordinate descent solver is used to find H and W. After extracting the non-negative components, columns of H, and up-sampling (i.e., resizing to the original image size to counter the effect of pooling layers) each component, it is processed by a Laplacian-of-Gaussian blob-detector to extract regions of the input image that are considered salient by CNN.

In the fourth stage, new input is mapped onto the previously learned components 1012 and the input is summarized by a histogram 1014 indicating the presence of various key components. This histogram provides a more detailed description of an activity. In prior work on image data, it was found that adding this histogram representation can reduce recognition errors by 42% (see Literature Reference No. 1).

Figure 11:
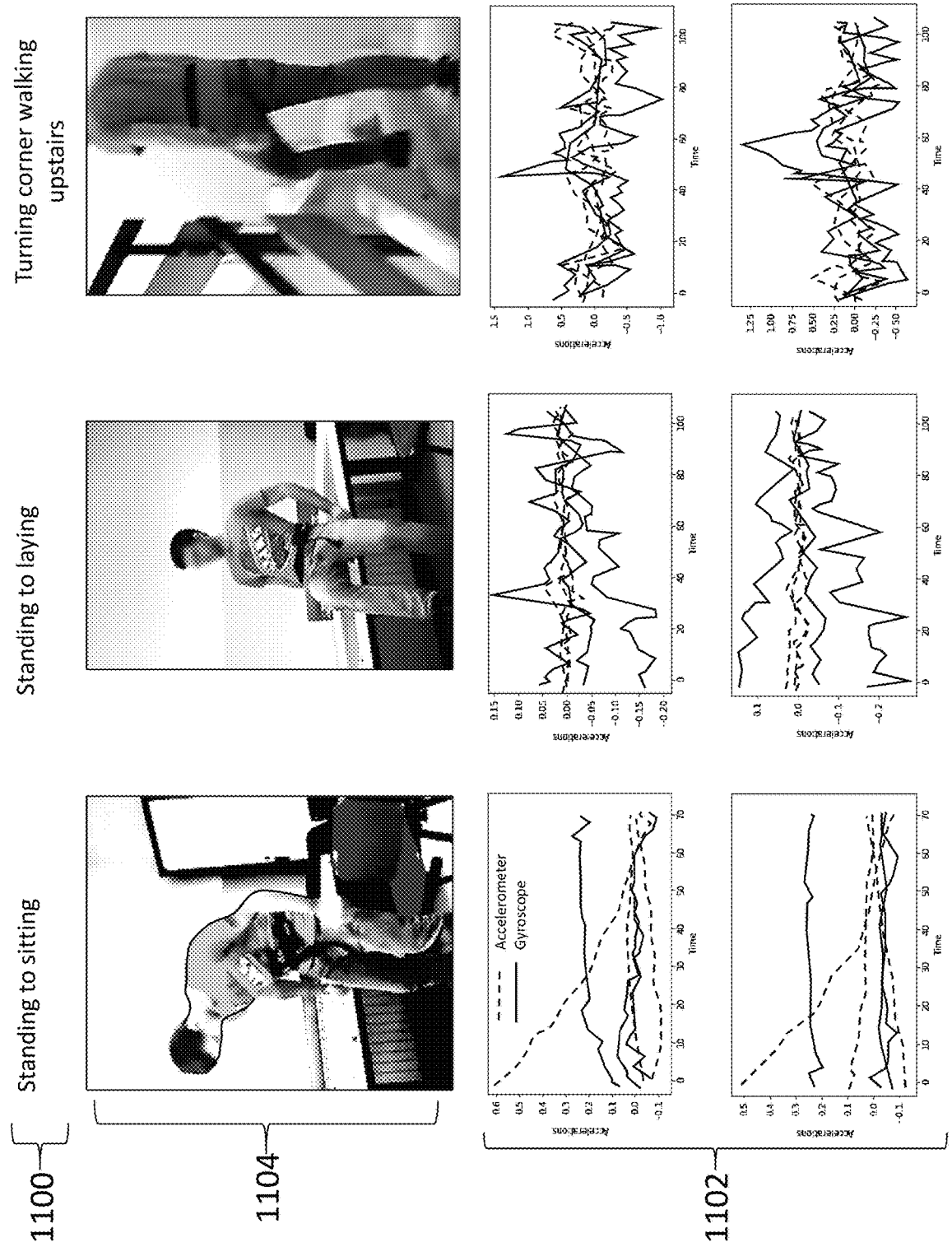
FIG. 11 is an illustration depicting samples of automatically identified activity components according to various aspects of the present invention.

For verification purposes, the above approach was also verified on biometric data. For example, the archived *Human Activity Recognition Using Smartphones Data Set* from University of California, Irvine, was used. The dataset contains accelerometer and gyroscope time-series data (3 channels each). The training data was split into six activities: walking, walking upstairs, walking downstairs, sitting, standing, and laying. The time-series data was converted into spectrograms and the DSL process pipeline of the present disclosure was used to extract activity components. As shown in FIG. 11, the method could indeed identify meaningful components in an unsupervised way. FIG. 11 depicts, for example, samples of automatically identified activity components 1100 through Deep Sense Learning that automatically extracts unlabeled activity components from biometric data 1102 (e.g., acceleration data as recorded by a mobile phone, etc.). For illustrative purposes, images 1104 are also provided depicting a user in performing the identified activity components 1100.

(4.3) Multi-Modal Disease Detection Component

Classification of multiple disease classes with a single detection paradigm is difficult because these disease classes may share overlapping symptomology, where the detection of a single physiological marker is not adequate to differentiate between classes. Additionally, disease classification may require the detection of disparate physiological markers, which is not possible with a single detection paradigm.

The system of this disclosure specifies the use of multiple detection modalities to find features for more accurate predictions of TBI, infectious disease, and mental states. Specifically, the system incorporates state-of-the-art, domain-specific detection methods using pupillometry, speech, and gait analysis, further details of which are provided below.

(4.3.1) Disease Detection from Speech Analysis

Figure 14:
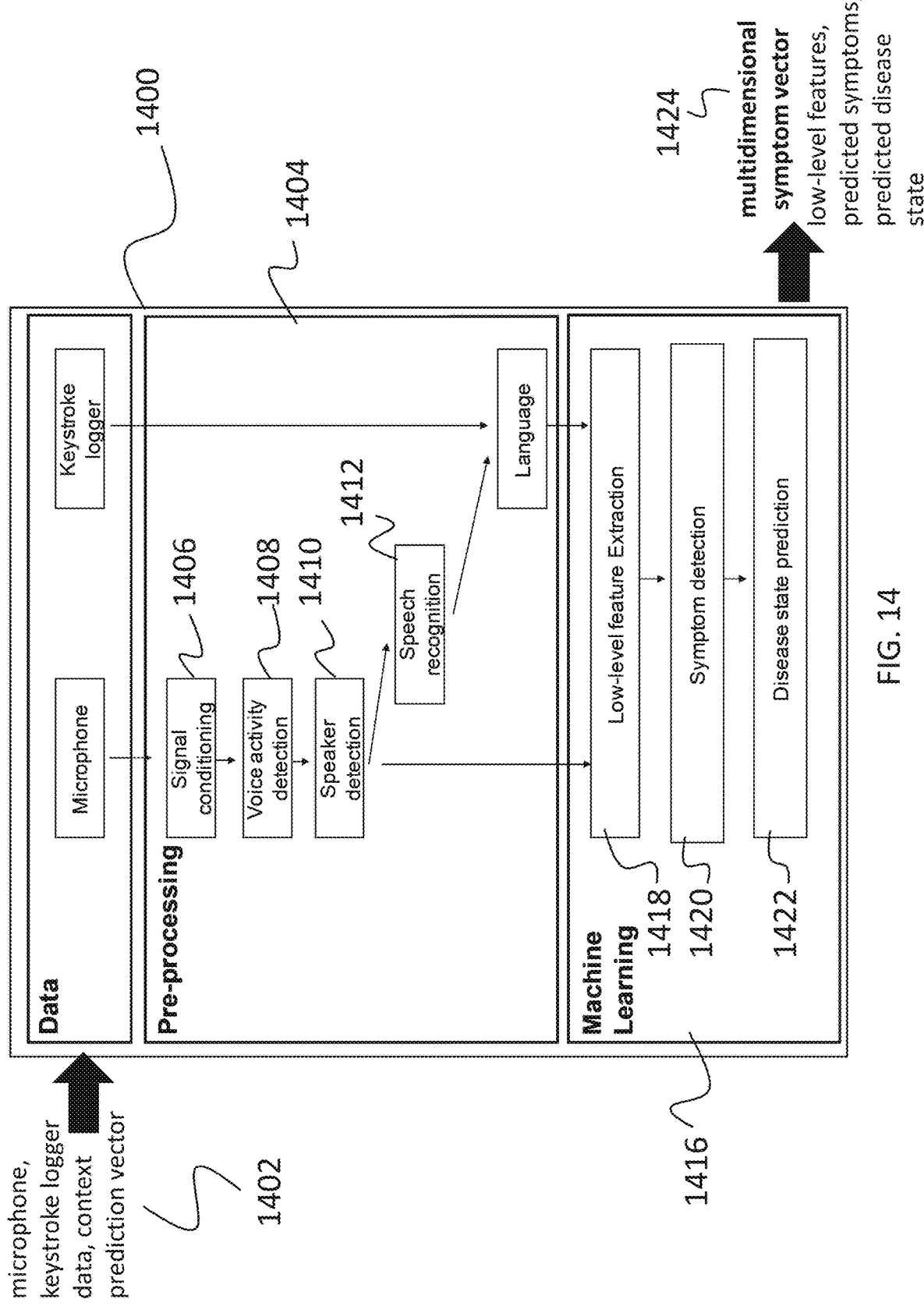
FIG. 14 is a flow chart illustrating a speech analysis subsystem according to various aspects of the present invention.

The system also includes a speech analysis subsystem. FIG. 14, for example, shows the process flow of the speech analysis subsystem. Leveraging and improving upon prior art (referenced below), this subsystem 1400 takes microphone data, keystroke logger data, and a context prediction vector as input 1402, and provides a multidimensional symptom vector as an output 1404 to the overall framework. To train the algorithms, an existing database of TBI speech, cough data, and pilot data can be used. The variety in speech samples allows the system to assess the health of voice, articulatory integrity and precision, and control and production of rhythm.

Acoustic data pre-processing 1404 for the subsystem 1400 includes four steps: signal conditioning 1406, voice activity detection 1408, speaker detection 1410, and automatic speech recognition 1412. A voice activity detector is applied to the raw audio data and identifies periods of silence (see Literature Reference No. 15 for a description of an example voice activity detector). The periods of silence are used to develop a background noise model that can be used during periods when the user is speaking to de-noise the speech. For this, the system uses noise reduction algorithms based on denoising autoencoders and simpler models based on spectral subtraction (see Literature Reference No. 16). Finally, to ensure that the system captures the correct speaker, it is assumed that there is some data available from user phone calls. This allows for development of a speaker-dependent model of speech production that is used to identify when the user is speaking during other times (see Literature Reference No. 17).

A series of machine learning 1416 tools are used for identifying speech features that provide diagnostic information for different neurological disorders (see Literature Reference Nos. 2, 7, and 12, and 18). These tools perform low-level feature extraction 1418, symptom detection 1420, and disease state prediction 1422.

(4.3.2) Activity and Disease Detection from Gait Analysis

The system of this disclosure can also be configured to detect activity and disease based on gait analysis. In this subsystem, an opportunistic learning framework is used for classification of physiological health states from gait analysis as well as feature production for DSL-based activity recognition. Here, the relevant data sources used are the accelerometer and gyroscope sensors as well as GPS coordinates (from the GPS unit) using the hardware of the mobile device (e.g., mobile phone, etc.). Prior art of network embedding (see Literature Reference Nos. 3-5, and 9) can be used to automatically learn the representation of entities via gait features and raw accelerometer/gyroscope/GPS data available. More importantly, different types of links within the Network of Networks (NoN) component can be leveraged to learn a set of representations that are most salient to identification of a disease state.

Figure 16:
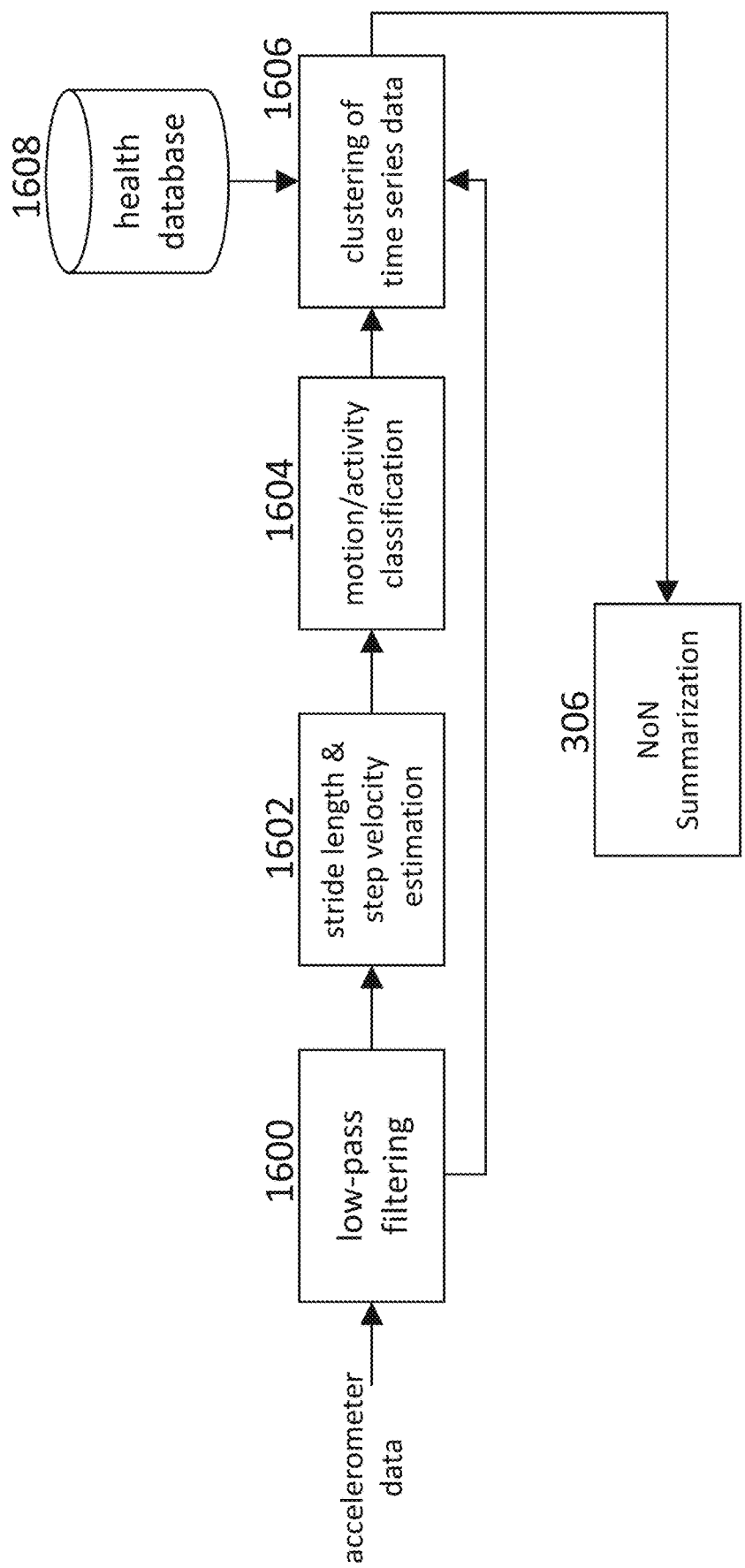
FIG. 16 is a flow chart illustrating a process for gait analysis according to various embodiments of the present invention.

First, automatic gait analysis performs stride detection followed by decomposition to divide a gait cycle into stance and swing periods, producing salient parameters of stride. The process (see FIG. 16) begins by smoothing and low-pass filtering 1600 the accelerometer data collected from the subject, followed by transforming the sensor coordinate system to the world coordinate system for stride length estimation and detection of step velocity 1602. Several other gait parameters can be further calculated, including: 1) stance time, 2) double support time, 3) mean stride frequency, 4) mean stride speed, and 5) mean stride cadence. Based on calculated gait parameters, motion/activity classification 1604 (walking, sitting, sleeping, walking fast, degradation in walking quality, etc.) is performed to feed and work in conjunction with DSL classification techniques (see DSL Component for Activity Recognition above).

To classify/predict health problems, the system first runs a clustering algorithm to group similar time series data together based on their disease biomarkers 1606 and other available health data that is already in a database 1608. Similarity between a pair of such time series data can be measured by dynamic time warping, despite mismatches in sampling rate or bit-depth. Each resulting cluster represents a possible physiological state, ranging from healthy to severe problems such as injury or illness. Further comparators, such as anomalies from baseline, or deviation from norm with similar cohorts can be used to further refine these diagnoses and return an output of disease state probability. These possible states are then incorporated into a model for the individual's physiological state, and then transferred as a network of features and prediction to the NoN Summarization framework described below.

(4.3.3) Disease Detection from Pupillometry

The system of this disclosure can also be used to detect diseases from pupillometry. Baseline pupil size data has long been shown to correlate with many factors including fatigue, lack of sleep, drug use, and stress (see Literature Reference Nos. 10 and 11. This subsystem involves opportunistic collection of RGB image data from a smartphone camera to distinguish pupil size trends over time with enough relative accuracy to reveal the same correlations with fatigue and lack of sleep as in previous studies. The subsystem comprises an algorithm that (1) understands the relative lighting condition from an image, (2) understands how inferred lighting affects expected pupil size, and (3) provides a measurement of deviation from this expectation. For example, the system can use the techniques specified by Rafiqi et al. (see Literature Reference No. 8), who established methods for inferring pupillary changes in response to task-evoked cognitive load, rather than changes in lighting.

Using convolutional neural network models, a time series of pupillary size can be inferred from the video snippets. These data are fed into a one-dimensional, many-to-one, convolutional neural network.

Figure 15:
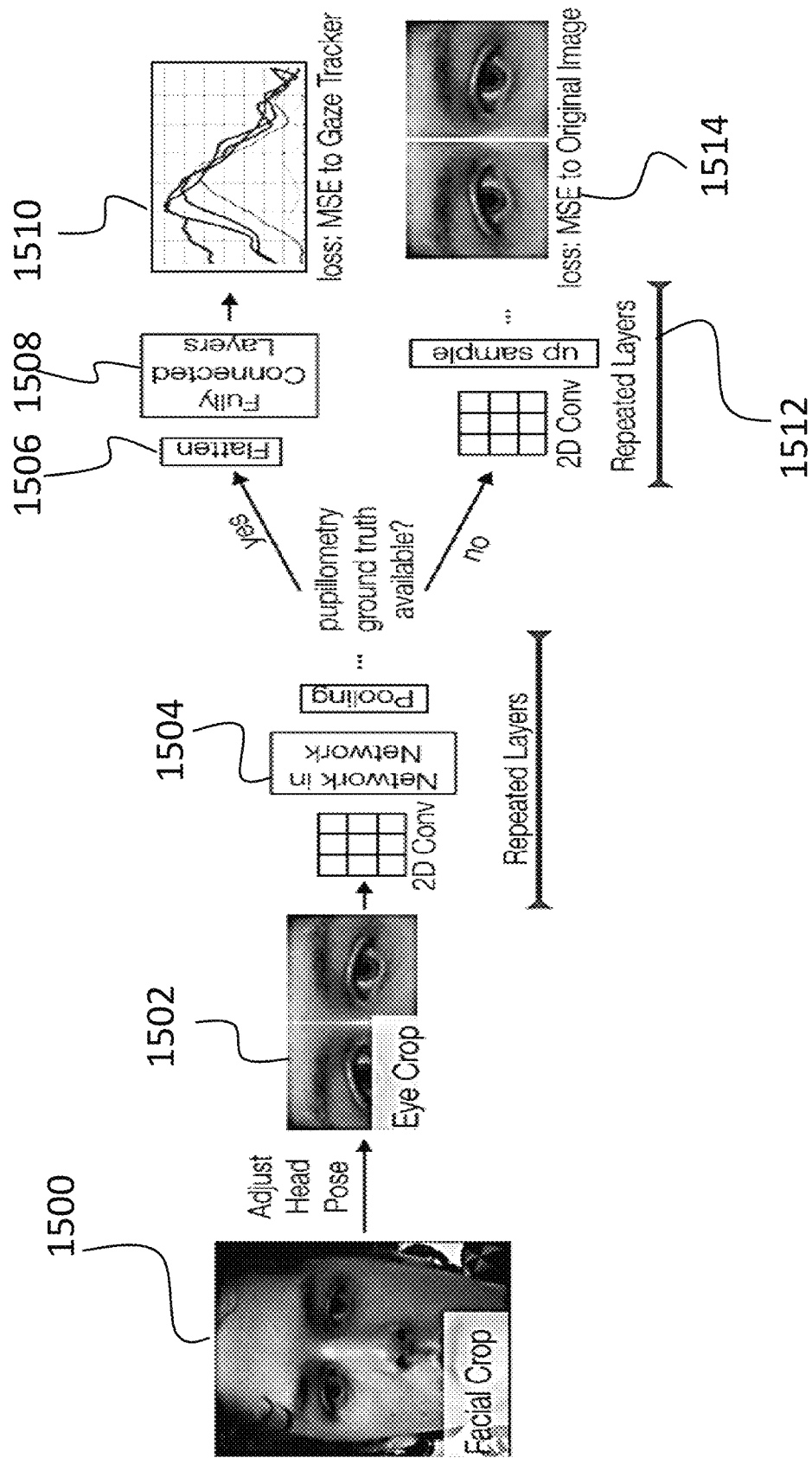
FIG. 15 is a flow chart illustrating a process for convolutional auto-encoding according to various aspects of the present invention.

To integrate unlabeled data, the system uses convolutional auto-encoding. In this scenario and as shown in FIG. 15, two different convolutional networks that share a common input branch are updated. After adjusting for facial crop 1500 and eye crop 1502, the input branch 1504 includes the original convolutional layers. When collected data is used for training (e.g., ground truth is available), the output feeds forward through flattening 1506 and fully connected dense layers 1508, and loss functions 1510 are generated from mean squared error to the ground truth pupil size at the final layer. When unlabeled data (e.g., ground truth not available) is fed into the network, the images pass through the same input convolutions (i.e., elements 1500, 1502, and 1504), but then split from the original network branch, feeding into convolutional up-sampling layers 1512. The final loss function 1514 is ascertained from the mean squared error in the final up-sampled image compared to the original eye images. FIG. 15 illustrates an example of this process as applied to pupillometry. The convolutional auto-encoding branch also serves as an additional regularization to the initial layers of the model.

By exploiting prior art in multiple sensing modalities (e.g., speech and cough analysis, gait analysis, and pupillometry analysis), the system of this disclosure provides a novel solution for multi-class disease detection. This component is integrated using the network of networks (NoN) summarization approach detailed in the next section.

(4.4) Network of Networks (NoN) Summarization Component

Multi-modal disease detection is challenging in that some analyses may be inconclusive and some analyses and hypotheses may be contradictory. Moreover, diseases are often diagnosed by how the measurements evolve over time, which adds another level of complexity. The NoN Summarization component of the present disclosure allows the incorporation of many different disease modalities and their progressions into a common detection paradigm and the ability to evaluate the totality of data available to determine co-morbidity, interaction effects, and best hypothesis selection.

The disease detection algorithms, discussed in the previous section, cover a wide range of disease specific domains. The diagnostic performance can be improved if these algorithms are combined in an optimal manner. The NoN approach described herein will automate the fusion of algorithms and data from different modalities, to 1) exceed performance compared to combining them with standard methods, 2) eliminate the need for human analysts to sift through massive amounts of data and algorithms, and 3) form the basis of a modality-agnostic framework to accept any effective disease family predictor.

NoN Summarization enables improved performance (increased disease identification accuracy) by extracting measures multi-modally across many layers of networks, which effectively narrow the scope of the analysis while accounting for different aspects of the disease detection algorithms. The main benefits are that: 1) incomplete data can be analyzed effectively; and 2) it provides a natural framework to evaluate multiple hypotheses and resolve conflicts.

Figure 12:
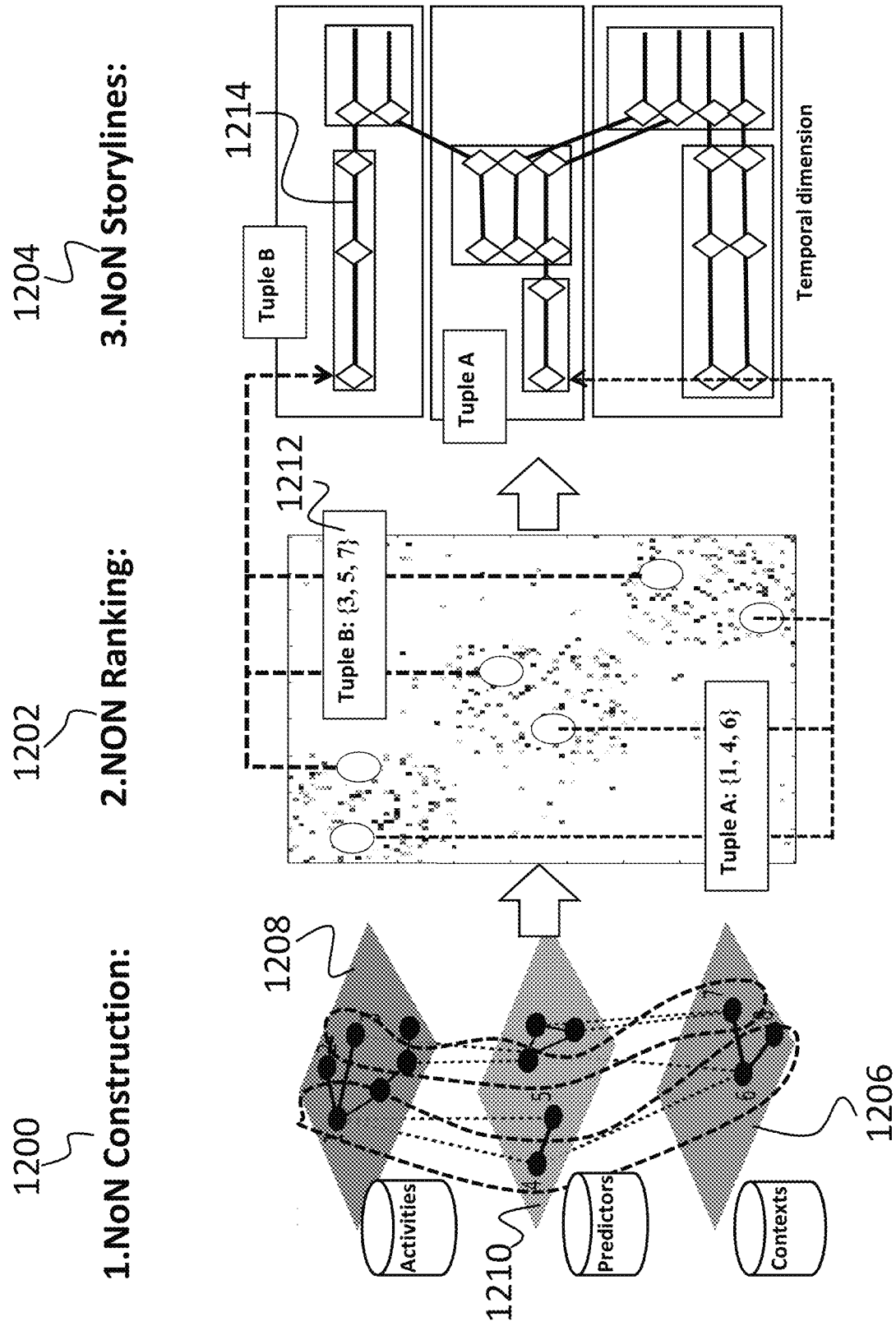
FIG. 12 is an illustration depicting a Network of Networks (NoN) summarization process according to various aspects of the present invention.

NoN Summarization is depicted in FIG. 12, which combines the features and outputs of multiple detection modalities to generate temporal motifs for the assessment of disease susceptibility and progression. NoN Summarization consists of three main innovations: First, NoN Construction 1200 of heterogeneous modalities utilizes efficient MapReduce decomposition to maximize parallel computing; Second, NoN Ranking 1202 selects nodes across the networks that simultaneously optimize importance, diversity, and coherence, with the coherent tuple grasshopper method; and Third, NoN Storylines 1204 tracks multiple symptom progressions that can parallel, merge, split, etc., by solving a modified longest path problem.

The first step is to construct the multilayer NoN 1200 that represents the multimodal input data for a disease group (i.e. TBI, biomarkers, associated activities, and disease descriptions). The context network layers 1206 represent the features from the data/measurements, where each node is the feature value/vector of a subject. Each context network layer 1206 corresponds to a feature type. Within each context network layer a pair of nodes are linked according to their similarity. A link between features (nodes) across layers indicates that the measurements correspond to the same subject taken at the same time stamp. Each node in the activity layer 1208 can be walking, sleeping, etc. and cross-layer links to nodes in this layer are given by the activity classification. Nodes in the predictor network layers 1210 come from domain expert disease state detection algorithms. One main challenge in NoN construction 1200 is the computational task of measuring pairwise node similarity in a large data set for features. This is addressed by using efficient MapReduce algorithms that exploit the parallel computing capability of Hadoop.

Next, NoN Ranking 1202 selects a set of top k-tuples in order to highlight certain indicators while covering the broad spectrum and variation of the disease. In other words, tuples 1212 are selected that are representative of multidomain disease detection. Each tuple 1212 contains a node (or plurality of nodes) from each network layer. The novelty is a coherent tuple grasshopper algorithm that simultaneously optimizes three objectives: diversity, importance, and coherence.

Diversity is used to cover different salient disease indicators. Importance attempts to find nodes that are central to their respective indicators. Coherence ensures that nodes from different data sources are closely related. At the high level, the NoN Ranking algorithm is a combination of two ideas: first, importance and diversity is achieved with a ranking algorithm (Algorithm 1) based on absorbing random walks. Second, tuple coherence is achieved with a stable matching algorithm.

Algorithm 1 provided below gives an overview of the ranking and tuple selection method. M=(V, E) is used to denote a multilayer graph with $(i, j, l_i, l_j) \in E$ denoting an edge between nodes $i \in V$ and $j \in V$ in layers $l_i$ and $l_j$, respectively. (It is assumed that each node only exists in a single layer.) An intra-layer edge is one in which $l_i = l_j$, and an inter-layer edge is one in which $l_i \neq l_j$. A tuple $(l_1, l_2, \ldots l_m)$ consists of a set of nodes in which $l_i \neq l_j$ for all $i, j \in \{l_1, l_2, \ldots l_m\}$ and for each $i \in \{l_1, l_2, \ldots l_m\}$, there exists a j $\in \{l_1, l_2, \ldots l_m\}$ such that $(i, j, l_i, l_j) E \in$.

A random walk on a single-layer graph G=(V, E) is a discrete-time stochastic process in which a walker in node v at time t transitions to node u at time t+1 along edge (v, u) with probability inversely proportional to the degree of node v. An absorbing random walk is a random walk in which there exist one or more nodes from which the walker cannot transition out of. Finally, the ranking algorithm uses a "fitness function" to determine the score of a tuple based on the elements' individual scores. For a tuple $(v_1, \ldots, v_l)$ spanning l layers, $f(v_1, \ldots, v_l)$ is used to denote this quantity.

Algorithm 1 NoN Ranking is provided as follows:
Input: Multilayer graph M=(V, E), tuple valuation function $f$ and integer k>0.
Output: Collection of k Tuples
1: Make M directed by replacing each undirected edge with two directed edges.
2: C←∅.
3: for all i=1, 2, . . . , k do
4: Rank the nodes in each layer (using only intra-layer links) according to their expected number of visits by a walker before reaching an absorbing node.
5: Find a tuple $(v_1, v_2, \ldots, v_l)$ whose elements are connected and maximize $f(v_1, v_2, \ldots, v_l)$.
6: C←C ∪ $\{v_1, v_2, \ldots v_l\}$.
7: Make nodes $v_1, v_2, \ldots, v_l$ absorbing nodes by replacing all out-going edges with self-loops.
8: end for
9: Return C The last step is NoN Storylines 1204, which is based on solving the longest path problem, to link tuples across multiple NoNs, ordered by time, to construct the storylines of disease progression. This process tracks multiple symptom progressions that can parallel, merge, split, etc., by solving a modified longest path problem. Each storyline 1214 needs to be succinct and consistent over time, and also allow merging and splitting of the individual storylines as they develop. The storylines, temporal motifs, which are the paths that link tuples in the temporal dimension, are used as templates to identify diseases through subgraph matching of the subjects' symptoms. Each temporal motif is a subgraph of the temporal NoN and consists of nodes that are linked across different layers (Tuples) and nodes that are linked across the temporal dimension.

To predict health problems, the system leverages available health data that is already in the database, for which the disease state is known/labeled. The storylines, temporal motifs, that correspond to these health data are the training data, which contain information about the disease state. The system then uses this to predict the disease state probability of new input health data that is not labeled.

Figure 13:
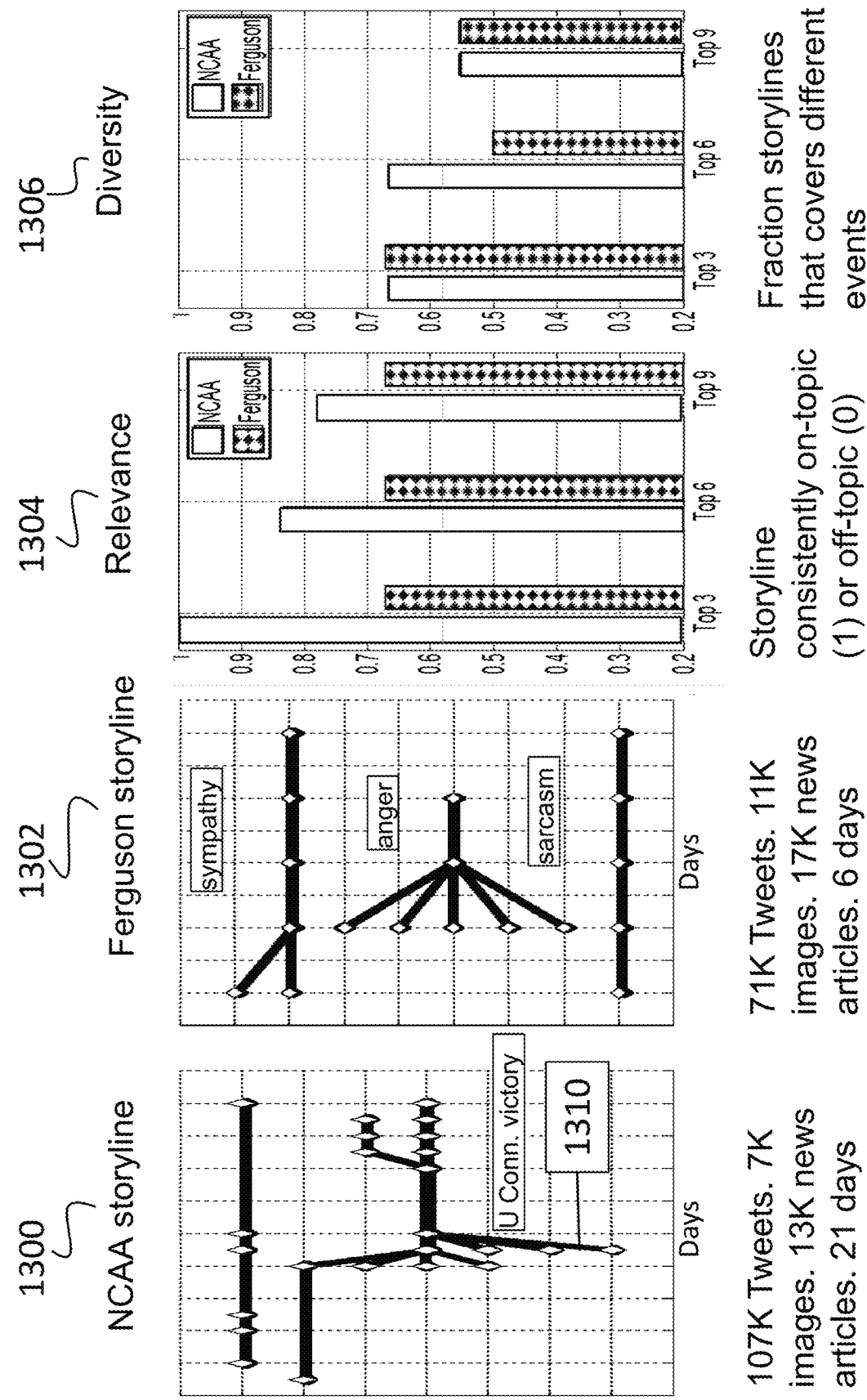
FIG. 13 is an illustration depicting storylines as generated according to various aspects of the present invention.

NoN Summarization was applied for event summarization, where it is able to provide good coverage of an event as it evolves over time. FIG. 13 shows the storylines generated for the 2014 NCAA "March Madness" collegiate basketball tournament 1300, and the 2014 Ferguson unrest 1302 following the fatal police shooting of Michael Brown, using multimodal datasets consisting of tweets, images, and new articles collected from open sources. The storylines exhibit some diversity in the form: some stories are more persistent, some are short-lived, some merge and split, indicating periods of convergence for otherwise distinct storylines. For example, one of the storylines 1310 for NCAA follows the University of Connecticut team's victory in the Final Four round. There are three parallel storylines corresponding to three major sentiments toward the event: sympathy, anger, and sarcasm. These storylines from our analysis show high relevance 1304 and good coverage (diversity 1306).

Since there is no ground truth, the relevance 1304 and diversity 1306 of the tweets/images/new articles that comprised each story were qualitatively assessed. For relevance 1304, each storyline was given a score of 1 or 0 depending on whether it was consistently on-topic or off-topic, respectively; these scores were then averaged for the top-k storylines. Similarly, the diversity 1306 of a collection of the top-k storylines was evaluated to reflect the fraction of storylines that covered the same prevailing sequence of events (i.e. how close the stories are to one another).

In summary, the ICAT reconstruction of sensor signals dramatically improves the quality of input data. Further, the DSL-based activity-recognition algorithm reduces recognition errors. This allows the system to employ multiple disease detection paradigms to improve diagnostic power. Using the multi-layer NoN architecture, the system exploits the multiple detection paradigms for automated cross-modal disease detection and dramatic improved detection accuracy over any existing state-of-the-art technologies.

As can be appreciated by those skilled in the art, if the system provides a prediction of a disease or infection, a variety of automated applications can be implemented. For example, the system can automatically notify 911, medics, etc. (via automated calling, messaging, etc.). If the detection is an infectious disease, the system can initiate a quarantine of the individual and automatically notify (via text, call, email messages, etc.) other people who may have been infected based on geolocation (GPS) proximity.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for health assessment, the system comprising:
a mobile device having one or more sensors, including at least one of an accelerometer, a geographic location sensor, and a camera;
wherein the mobile device includes at least one or more processors and a memory, the memory being a non-transitory computer-readable medium having executable instructions encoded thereon, such that upon execution of the instructions, the one or more processors perform operations of:
obtaining sensor data related to an operator of the mobile device from the one or more sensors;
generating a network of networks (NoN) based on the sensor data, the NoN having a plurality of layers with linked nodes;
generating tuples, where each tuple contains a node from each layer that optimizes importance, diversity, and coherence;
generating storylines based on the tuples that solves a longest path problem for each tuple, the storylines tracking multiple symptom progressions of the operator; and
generating a disease prediction of the operator based on the storylines.

2. The system as set forth in claim 1, wherein the plurality of layers includes a context layer, a predictor layer, and an activity layer, the context layer representing features within the sensor data, the activity layer representing detected activities of the operator based on the sensor data, and the predictor layer representing domain knowledge regarding at least one disease.

3. The system as set forth in claim 2, wherein each node within the context layer is a feature value of the operator, and where pairs of nodes are linked according to their similarity such that a link between feature nodes indicates that feature measurements corresponds to the operator taken at a common time stamp.

4. The system as set forth in claim 2, wherein each node within the activity layer is an activity classification of the operator, and where pairs of nodes are linked according to their similarity such that a link between activity nodes indicates that activity classification corresponds to the operator taken at a common time stamp.

5. The system as set forth in claim 2, wherein each node within the predictor layer is a disease classification based on domain knowledge.

6. The system as set forth in claim 1, wherein the storylines are temporal motifs, where each temporal motif is a subgraph of the NoN that comprises nodes that are linked across different tuples and nodes that are linked across a temporal dimension.

7. A computer program product for health assessment, the computer program product comprising:
a non-transitory computer-readable medium having executable instructions encoded thereon, such that upon execution of the instructions by one or more processors, the one or more processors perform operations of:
obtaining sensor data related to an operator of a mobile device from one or more sensors embedded in the mobile device;
generating a network of networks (NoN) based on the sensor data, the NoN having a plurality of layers with linked nodes;
generating tuples, where each tuple contains a node from each layer that optimizes importance, diversity, and coherence;
generating storylines based on the tuples that solves a longest path problem for each tuple, the storylines tracking multiple symptom progressions of the operator; and
generating a disease prediction of the operator of the mobile device based on the storylines.

8. The computer program product as set forth in claim 7, wherein the plurality of layers includes a context layer, a predictor layer, and an activity layer, the context layer representing features within the sensor data, the activity layer representing detected activities of the operator based on the sensor data, and the predictor layer representing domain knowledge regarding at least one disease.

9. The computer program product as set forth in claim 8, wherein each node within the context layer is a feature value of the operator, and where pairs of nodes are linked according to their similarity such that a link between feature nodes indicates that feature measurements corresponds to the operator taken at a common time stamp.

10. The computer program product as set forth in claim 8, wherein each node within the activity layer is an activity classification of the operator, and where pairs of nodes are linked according to their similarity such that a link between activity nodes indicates that activity classification corresponds to the operator taken at a common time stamp.

11. The computer program product as set forth in claim 8, wherein each node within the predictor layer is a disease classification based on domain knowledge.

12. The computer program product as set forth in claim 7, wherein the storylines are temporal motifs, where each temporal motif is a subgraph of the NoN that comprises nodes that are linked across different tuples and nodes that are linked across a temporal dimension.

13. A computer implemented method for health assessment, the method comprising an act of:
causing one or more processors to execute instructions encoded on a non-transitory computer-readable medium, such that upon execution, the one or more processors perform operations of:

obtaining sensor data related to an operator of a mobile device from one or more sensors embedded in the mobile device;

generating a network of networks (NoN) based on the sensor data, the NoN having a plurality of layers with linked nodes;

generating tuples, where each tuple contains a node from each layer that optimizes importance, diversity, and coherence;

generating storylines based on the tuples that solves a longest path problem for each tuple, the storylines tracking multiple symptom progressions of the operator; and generating a disease prediction of the operator of the mobile device based on the storylines.

14. The method as set forth in claim 13, wherein the plurality of layers includes a context layer, a predictor layer, and an activity layer, the context layer representing features within the sensor data, the activity layer representing detected activities of the operator based on the sensor data, and the predictor layer representing domain knowledge regarding at least one disease.

15. The method as set forth in claim 14, wherein each node within the context layer is a feature value of the operator, and where pairs of nodes are linked according to their similarity such that a link between feature nodes indicates that feature measurements corresponds to the operator taken at a common time stamp.

16. The method as set forth in claim 14, wherein each node within the activity layer is an activity classification of the operator, and where pairs of nodes are linked according to their similarity such that a link between activity nodes indicates that activity classification corresponds to the operator taken at a common time stamp.

17. The method as set forth in claim 14, wherein each node within the predictor layer is a disease classification based on domain knowledge.

18. The method as set forth in claim 13, wherein the storylines are temporal motifs, where each temporal motif is a subgraph of the NoN that comprises nodes that are linked across different tuples and nodes that are linked across a temporal dimension.

* * * * *